US012763222B2

(12) United States Patent
Stanojevic et al.

(10) Patent No.: US 12,763,222 B2
(45) Date of Patent: Oct. 13, 2026

(54) SYSTEMS AND METHODS FOR AI CARE MANAGEMENT

(71) Applicant: Ellipsis Health, Inc., San Francisco, CA (US)

(72) Inventors: Marija Stanojevic, Toronto (CA); Craig Stephen Randall, San Juan Capistrano, CA (US); Michael Aratow, Mountain View, CA (US); Elizabeth Ellen Shriberg, Berkeley, CA (US); Melissa McCool, Encinitas, CA (US); Mainul Mondal, San Francisco, CA (US)

(73) Assignee: Ellipsis Health, Inc., San Francisco, CA (US)

( * ) Notice: Subject to any disclaimer, the term of this patent is extended or adjusted under 35 U.S.C. 154(b) by 0 days.

(21) Appl. No.: 19/418,672

(22) Filed: Dec. 12, 2025

(65) Prior Publication Data

US 2026/0171263 A1 Jun. 18, 2026

Related U.S. Application Data

(60) Provisional application No. 63/733,919, filed on Dec. 13, 2024.

(51) Int. Cl.
*G06F 16/245* (2019.01)
*G06V 10/40* (2022.01)
(Continued)

(52) U.S. Cl.
CPC ............. *G16H 80/00* (2018.01); *G06V 10/40* (2022.01); *G06V 40/10* (2022.01); *G10L 13/027* (2013.01); *G10L 15/183* (2013.01); *G10L 15/22* (2013.01); *G10L 25/66* (2013.01); *G10L 2015/223* (2013.01)

(58) Field of Classification Search
CPC ..... G06F 16/245; G06F 16/248; G10L 15/22; A61B 5/74
See application file for complete search history.

(56) References Cited

U.S. PATENT DOCUMENTS

| | | | | |
|---|---|---|---|---|
| 2019/0214127 A1* | 7/2019 | Hu | ............................ | G06T 5/70 |
| 2019/0216333 A1* | 7/2019 | Lai | .......................... | G06F 16/51 |

(Continued)

FOREIGN PATENT DOCUMENTS

| | | | | |
|---|---|---|---|---|
| IN | 202441060375 A * | 8/2024 | ............. | G06F 11/10 |
| WO | WO-2014145149 A1 | 9/2014 | | |
| WO | WO-2021033886 A1 | 2/2021 | | |

OTHER PUBLICATIONS

Patent Cooperation Treaty, International Search Report and Written Opinion issued for PCT Application No. PCT/US2025/059467, dated Feb. 18, 2026, 10 pages.

*Primary Examiner* — Daniel Abebe
(74) *Attorney, Agent, or Firm* — Norton Rose Fulbright US LLP

(57) ABSTRACT

According to an aspect, there is provided systems and methods to drive a conversation with a user. The method includes receiving conversational data from a user, embedding the conversational data, generating a reply using a response-generating AI to process the embedded conversational data and context from the knowledge base with the foundational model (e.g., LLM, multimodal, world model), and transmitting the generated reply.

19 Claims, 6 Drawing Sheets

(51) Int. Cl.

| | |
|---|---|
| ***G06V 40/10*** | (2022.01) |
| ***G10L 13/027*** | (2013.01) |
| ***G10L 15/183*** | (2013.01) |
| ***G10L 15/22*** | (2006.01) |
| ***G10L 25/66*** | (2013.01) |
| ***G16H 80/00*** | (2018.01) |

(56) References Cited

U.S. PATENT DOCUMENTS

2022/0129724 A1 4/2022 Feinson et al.
2022/0391600 A1* 12/2022 Qi .......................... G06F 40/30
2024/0403367 A1* 12/2024 Dressler, II ............. G06F 40/35
2025/0238451 A1* 7/2025 Sharma ................... G06F 40/40
2025/0345009 A1* 11/2025 Vakili .................... A61B 5/741
2025/0384019 A1* 12/2025 Schirmer ............ G06F 16/2237

* cited by examiner

SYSTEMS AND METHODS FOR AI CARE MANAGEMENT

CROSS REFERENCE

This application claims priority from U.S. Provisional Patent Application No. 63/733,919, entitled "SYSTEMS AND METHODS FOR AI CARE MANAGEMENT", filed on Dec. 13, 2024, the entire contents of which are incorporated herein by reference.

FIELD

The present disclosure generally relates to the field of clinical care management, and more specifically, embodiments relate to devices, systems, and methods for implementing artificial intelligence assisted clinical care management.

INTRODUCTION

Healthcare care managers carry out an important function within the healthcare system. These care managers may be responsible for following up with patients with chronic care needs, post-operative care needs, behavioral health needs, or other needs. These care managers can be responsible for collecting data on the patients, providing support to the patients, answering questions for the patients, or providing access to other resources for the patients.

However, these care management calls take time and require trained personnel. The administrative aspects of the care manager's role can take up a significant portion of their time on calls with patients. This can lead to a reduced focus on delivering support to the patient. It can also be difficult to standardize the care offered by the care managers to ensure that every patient is receiving the optimum standard of care.

Furthermore, the number of agents available and their availability during certain hours is finite. It may be challenging for an agent to follow up with sufficient frequency to provide timely health support. Hiring more agents may prove to be costly which may increase the overall cost of healthcare and divert resources to the employ of additional agents rather than to the provision of health services to the patients.

Improvement in the field of patient care/care management is needed.

SUMMARY

Described herein are systems and methods to provide an artificial intelligence driven care manager (AI Care Manager) to supplement the work of the human care managers. Such AI Care Managers can take the place or augment conventional care managers for patient calls. These AI Care Managers can run through questionnaires with the patients to obtain follow-up information from the client. The AI Care Managers can be configured to process follow-up tasks (e.g., scheduling another meeting, ordering drug refills, scheduling appointments with a physician or specialist, providing diet advice, directing medication usage, ensuring compliance with healthcare team instructions, predicting flow of next steps in patient's care, etc.). The AI Care Manager can supplement human agents which may reduce the administrative burden of repetitive and time-consuming tasks, improve program enrollment while decreasing acquisition costs, improve resource utilization, and enhance engagement. The systems described herein may provide care management at scale with consideration for a growing range of patient demographics (e.g. spoken language and translation/transcription, those with disabilities such as deafness/blindness, etc.).

According to an aspect, there is provided a system to drive a conversation with a user. The system including a hardware processor including a response-generating AI that may include a knowledge base and/or an LLM, a multimodal, and/or a world model, (e.g., foundational models that can work with, for example, video, text, and audio together) and memory for storing instructions executable by the hardware processor. When executed, the instructions cause the system to receive conversational data from a user, embed the conversational data, generate a reply using a response-generating AI to process the embedded conversational data and context from the knowledge base, transmit the generated reply.

In some embodiments, the system further includes a vocal biomarker engine configured to predict whether the user has a physical, mental, or behavioural health condition or the severity of same.

In some embodiments, the system is further configured to predict one or more of global states of the user, moment-to-moment states of the user, context of a user environment.

In some embodiments, the instructions further cause the system to determine utility of the generated reply based on subsequent conversational data and to update the response-generating AI based on the utility of the generated reply.

In some embodiments, the system further includes a process engine configured to generate and act on tasks based on the conversation.

In some embodiments, the process engine is configured to generate and act on the tasks based on patient information.

In some embodiments, the process engine is configured to interface with external systems to retrieve the patient information or to act on the tasks.

In some embodiments, the response-generating AI processes the embedded conversational data using cached conversational data, wherein the cached conversational data comprises prior embedded conversational data provided by the user.

In some embodiments, the context includes a conversational objective and a conversational task, the conversational task is used to generate the reply and the conversational objective is a goal of the conversation, and the instructions cause the system to determine utility of the generated reply in achieving the conversational objective based on subsequent conversational data, and update the conversational tasks based on the utility of the generated reply.

In some embodiments, transmitting the generated reply comprises providing the generated reply to a human agent, wherein the generated reply is a suggested next response or action or direction.

In some embodiments, transmitting the generated reply comprises delivering the generated reply to the user.

In some embodiments, the response-generating AI is configured to access electronic medical records.

In some embodiments, the response-generating AI is configured to use patient healthcare metadata.

In some embodiments, the conversational data is processed by an input guardrail to classify the conversational data as bad or good.

In some embodiments, the input guardrail processes the conversational data by determining that the conversational data exhibits one or more of unintelligibility, inappropriate behaviour, and inappropriate topic.

In some embodiments, the conversational data is embedded when the conversational data is classified as good or the input guardrail carries out remediation when the conversational data is classified as bad. Optionally, the input guardrail redirects the conversation to a human agent upon classifying the conversation data as bad. Optionally, the conversation data is classified as bad after remediation fails. Optionally, the human agent is provided with a summary of the conversation and/or a summary of a reason for the bad classification.

In some embodiments, the generated reply is processed by an output guardrail to classify the generated reply as good or bad In some embodiments, the output guardrail processes the generated reply by determining that the generated reply exhibits one or more of unresponsiveness, inaccuracy, harmful information, and inappropriate topic.

In some embodiments, the generated reply is transmitted to the user when the generated reply is classified as good or the output guardrail carries out remediation when the generated reply is classified as bad. Optionally, the output guardrail redirects the conversation to a human agent upon classifying the conversation data as bad. Optionally, the conversation data is classified as bad after remediation fails. Optionally, the human agent is provided with a summary of the conversation and/or a summary of a reason for the bad classification.

In some embodiments, the response-generating AI is pre-loaded with context from one or more of prior conversations with the user, health records about the user, conversational objectives.

In some embodiments, the conversational data is converted to text using an automatic speech recognition engine.

In some embodiments, the generated reply is converted to speech using a text-to-speech engine that can provide the generated speech as one of a plurality of custom voices.

In some embodiments, the system is configured to elicit information for or provide information on one or more of medication reconciliation, diet, exercise, social determinants of health, living situation, assessment of severity of depression and anxiety symptomatology, substance use, assessment of cognitive availability, assessment of ability to perform activities of daily living, care pathways, clinical protocols, claims eligibility, claims adjustment, claims dispute, claims issues, pharmaceutical benefits, prior authorizations, and pre-admission, post-discharge, and ongoing care management factors, or the like.

In some embodiments, the system is used for one or more of a medical follow up conversation, a patient intake conversation, an insurance intake conversation, or a troubleshooting technology conversation.

In some embodiments, the response-generating AI accesses a user profile comprising user preferences or personalizations to tailor the generated reply or the conversation.

In some embodiments, the personalizations in the user profile are set by a healthcare professional in the clinical workflow.

In some embodiments, the conversational data includes spoken language, text, or video.

In some embodiments, the system is configured to be multilingual. Optionally, the system detects a language of the conversational data prior to embedding the conversational data and uses the detected language to embed the conversational data, select an embedding model, response-generating AI, input guardrail, or output guardrail, or translate the conversational data.

Some embodiments further include a sensing engine configured to assess the user.

In some embodiments, the sensing engine receives a captured image of the user, processes the captured image with an image processing model to extract features from the captured image, processes the extracted features to generate a user assessment; and transmits the user assessment to the response-generating AI.

According to an aspect, there is provided a method to drive a conversation with a user. The method includes receiving conversational data from a user, embedding the conversational data, generating a reply using a response-generating AI to process the embedded conversational data and context from the knowledge base, and transmitting the generated reply.

In some embodiments, the method further includes predicting whether the user has a physical, mental, or behavioural health condition or the severity of same using the conversational data.

In some embodiments, the method further includes predicting one or more of global states of the user, moment-to-moment states of the user, context of a user environment.

In some embodiments, the method further includes determining utility of the generated reply based on subsequent conversational data and updating the response-generating AI based on the utility of the generated reply.

In some embodiments, the method further includes generating and actioning tasks based on the conversation.

In some embodiments, the tasks are generated and actioned based on patient information.

In some embodiments, the response-generating AI processes the embedded conversational data using cached conversational data, wherein the cached conversational data comprises prior embedded conversational data provided by the user.

In some embodiments, the context includes a conversational objective and a conversational task, the conversational task is used to generate the reply and the conversational objective is a goal of the conversation, and the method further includes determining utility of the generated reply in achieving the conversational objective based on subsequent conversational data and updating the conversational tasks based on the utility of the generated reply.

In some embodiments, transmitting the generated reply comprises providing the generated reply to a human agent, wherein the generated reply is a suggested next response or action or direction.

In some embodiments, transmitting the generated reply comprises delivering the generated reply to the user.

In some embodiments, the response-generating AI is configured to access electronic medical records.

In some embodiments, the response-generating AI is configured to use patient healthcare metadata.

In some embodiments, the conversational data is processed by an input guardrail to classify the conversational data as bad or good.

In some embodiments, the input guardrail processes the conversational data by determining that the conversational data exhibits one or more of unintelligibility, inappropriate behaviour, and inappropriate topic.

In some embodiments, the conversational data is embedded when the conversational data is classified as good or the input guardrail carries out remediation when the conversational data is classified as bad. Optionally, the input guardrail redirects the conversation to a human agent upon classifying the conversation data as bad. Optionally, the conversation data is classified as bad after remediation fails. Optionally, the human agent is provided with a summary of the conversation and/or a summary of a reason for the bad classification.

In some embodiments, the generated reply is processed by an output guardrail to classify the generated reply as good or bad In some embodiments, the output guardrail processes the generated reply by determining that the generated reply exhibits one or more of unresponsiveness, inaccuracy, harmful information, and inappropriate topic.

In some embodiments, the generated reply is transmitted to the user when the generated reply is classified as good or the output guardrail carries out remediation when the generated reply is classified as bad. Optionally, the output guardrail redirects the conversation to a human agent upon classifying the conversation data as bad. Optionally, the conversation data is classified as bad after remediation fails. Optionally, the human agent is provided with a summary of the conversation and/or a summary of a reason for the bad classification.

In some embodiments, the response-generating AI is pre-loaded with context from one or more of prior conversations with the user, health records about the user, conversational objectives.

In some embodiments, the conversational data is converted to text using an automatic speech recognition engine.

In some embodiments, the generated reply is converted to speech using a text-to-speech engine that can provide the generated speech as one of a plurality of custom voices.

In some embodiments, the method is configured to elicit information for or provide information on one or more of medication reconciliation, diet, exercise, social determinants of health, living situation, assessment of severity of depression and anxiety symptomatology, substance use, assessment of cognitive availability, assessment of ability to perform activities of daily living, care pathways, clinical protocols, claims eligibility, claims adjustment, claims dispute, claims issues, pharmaceutical benefits, prior authorizations, and pre-admission, post-discharge, and ongoing care management factors, or the like.

In some embodiments, the method is used for one or more of a medical follow up conversation, a patient intake conversation, an insurance intake conversation, or a troubleshooting technology conversation.

In some embodiments, the response-generating AI accesses a user profile comprising user preferences or personalizations to tailor the generated reply or the conversation.

In some embodiments, the personalizations in the user profile are set by a healthcare professional in the clinical workflow.

In some embodiments, the conversational data includes spoken language, text, or video.

In some embodiments, the method is configured to be multilingual. Optionally, the method further includes detecting a language of the conversational data prior to embedding the conversational data and using the detected language to embed the conversational data, select an embedding model, response-generating AI, input guardrail, or output guardrail, or translate the conversational data.

In some embodiments, the method further includes assessing the user using a sensing engine.

In some embodiments, the method further includes receiving a captured image of the user, processing the captured image with an image processing model to extract features from the captured image, processing the extracted features to generate a user assessment, and transmitting the user assessment to the response-generating AI.

Many further features and combinations thereof concerning embodiments described herein will appear to those skilled in the art following a reading of the instant disclosure.

DESCRIPTION OF THE FIGURES

In the figures.

DETAILED DESCRIPTION

Described herein are systems and methods to provide an artificial intelligence driven care manager (AI Care Manager) to supplement the work of the human care managers (e.g., human agents). Such AI Care Managers can take the place of human agents for patient calls. These AI Care Managers can run through scripts with the patients to obtain follow-up information from the client. The AI Care Managers can be configured to process follow-up tasks (e.g., scheduling another meeting, ordering drug refills, scheduling appointments with a physician or specialist, providing diet advice, directing medication usage, ensuring compliance with healthcare team instructions, etc.). The AI Care Manager can supplement human agents which may reduce the administrative burden of repetitive and time-consuming tasks, improve program enrollment while decreasing acquisition costs, improve resource utilization, and enhance engagement.

Such AI Care Managers may be effective in many different applications. For example, the AI Care Managers may be configured to provide clinical follow-up for patients post-discharge (e.g., to see if they are taking their medications, to follow up regarding the presentation of additional symptoms, organize transportation, etc.). The AI Care Managers may also be configured to help patients enroll in, for example, health programs (e.g., talk about the claims in the program and answer any questions, etc.). The AI Care Managers may also be effective to populate surveys by interviewing the patient (e.g., health risk assessments, surveys for regulatory programs, reimbursement surveys (e.g., for life insurance or disability), etc.).

Some technical advantages of the systems and methods described herein include reducing the administrative cost of healthcare by reducing the number of human agents required. They may also provide timely, consistent, and accurate information to patients. They may provide more standardized service across a wide array of disparate patient types.

General System Architecture

Figure 1A:
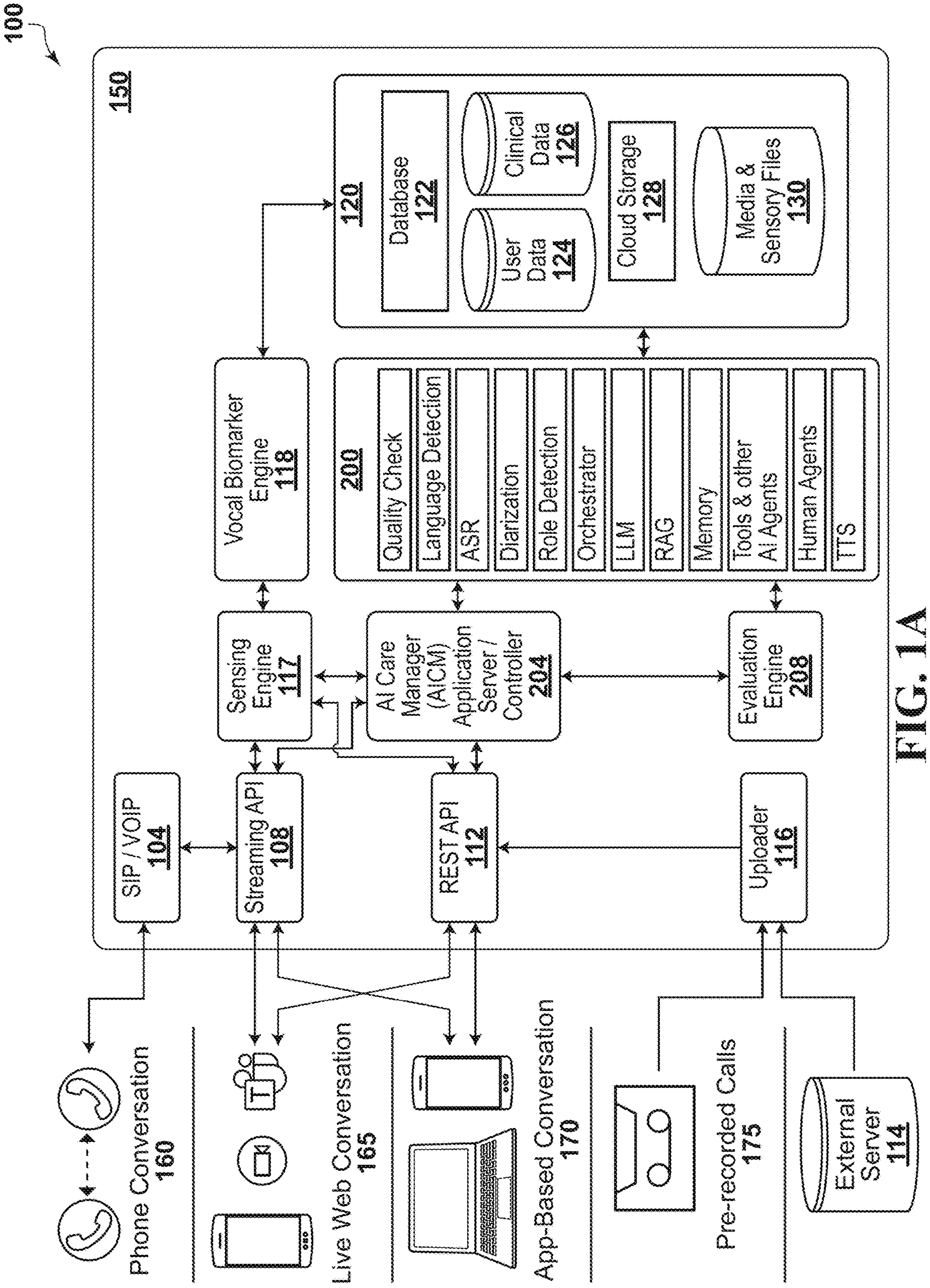
FIG. 1A shows an example system architecture implementing an AI Care Manager, according to some embodiments.

FIG. 1A shows an example system architecture 100 implementing an AI Care Manager engine 200, according to some embodiments.

The system 100 can provide access by users (e.g., patients) to an AI Care Manager engine 200 configured to carry out, for example, healthcare-related tasks and discussions. The AI Care Manager engine 200 can supplement a human agent 240 by running through questionnaires with the user or providing instructions or information to the user. In some embodiments, the AI Care Manager engine 200 can also help enroll the user into programs and/or arrange assistance for the user (e.g., with ordering their medications, transportation arrangements, etc.). The AI Care Manager engine 200 can engage in bi-directional communication so that the AI Care Manager engine 200 can pursue appropriate action with the patient given the conversational information (e.g., action the information received). In some embodiments, the conversations with the AI Care Manager engine 200 can analyze a user using sensing inputs (e.g., video, etc.) using a sensing engine 117 to retrieve more information from the user (e.g., assess their posture, demeanor, unconscious movement, etc.). In some embodiments, the conversations with the AI Care Manager engine 200 can analyze a user using a vocal biomarker engine 118 (e.g., which may be a subset of or related to the sensing engine 117) to retrieve more information about the user (e.g., assess the user using their language and acoustic information). In some embodiments, the AI Care Manager engine 200 can change the nature of current conversation in order to increase engagement with the patient and to drive timely outcomes (e.g. pursue more symptoms in their original context, etc.) by having the capability to understand the subject's words and how the patient may convey those words. In some embodiments, the AI Care Manager engine 200 can take real-time action.

The system 100 can include the computing device 150 configured to enable the use of a telephone 160, live web conversations 165, an app 174 on user device 170, or pre-recorded calls 175 to access the AI Care Manager engine 200. The computing device 150 can further permit access by a human agent 240 (e.g., an operator or administrator) through, for example, an app 184 on agent device 180. The computing device 150 can optionally receive configuration data from external servers, such as an external server 114.

Figure 1B:
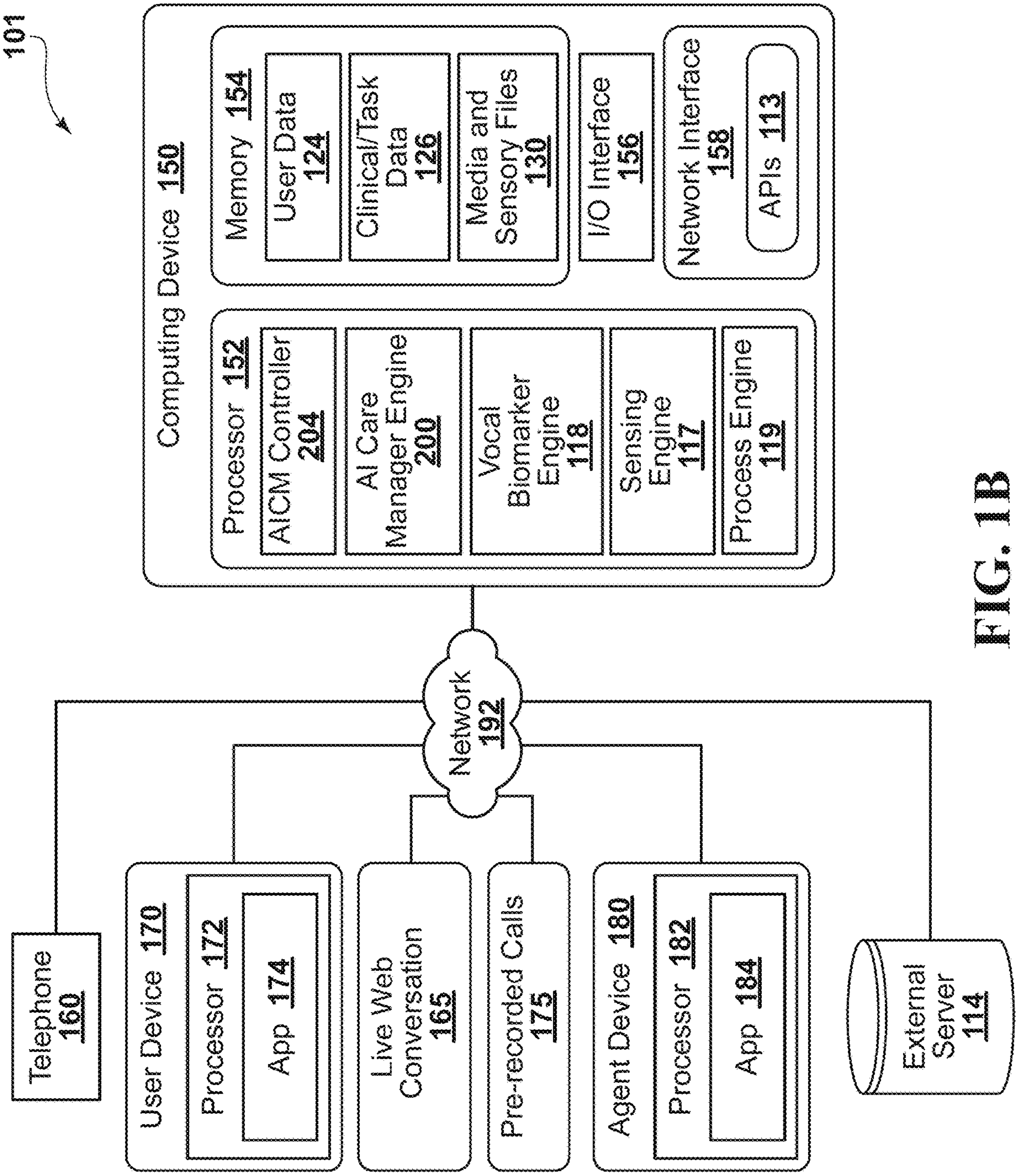
FIG. 1B shows another example of system architecture implementing an AI Care Manager, according to some embodiments.

For example, and without limitation, the computing device 150 may be a server, network appliance, set-top box, embedded device, computer expansion module, personal computer, laptop, personal data assistant, cellular telephone, smartphone device, UMPC tablets, video display terminal, gaming console, electronic reading device, wireless hypermedia device, cloud platforms, high-performance computing servers, and virtual image, container, managed computer environments or any other computing device capable of being configured to carry out the methods described herein The computing device 150 can include a processor 152 (see FIG. 1B), storage 120, an I/O interface 156 (see FIG. 1B), and a network interface 158 (see FIG. 1B). The computing device can be configured with a streaming API 108, a REST API 112, an uploader 116, an AI Care Manager engine 200, a sensing engine 117 (e.g., with a vocal biomarker engine 118).

The processor 152 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. In some embodiments, the processor 152 may be, for example a GPU or a CPU (or clusters thereof) in its runtime environment.

A SIP/VoIP engine 104 can be configured to enable the communication by telephone 160 over internet protocol networks such as the Internet. The SIP/VoIP engine 104 may be provided where the conversation with the user is carried out over telephone 160. The SIP/VoIP engine 104 can convert any conversations that occur via telephony or other multimedia formats into a format transmissible by Internet Protocol before sending through the network. In some embodiments, the system may make use a more specialized (and VoIP-based) WebRTC environment.

The streaming API 108 can be configured to enable an app-based conversation and phone-based conversation. The streaming API 108 can be configured to receive, process, and return requests from a telephone 160 and/or a user device 170 (see FIG. 1B). The computing device 150 may be configured to process information from a user device 170 in a different manner than through a REST API 112.

The REST API 112 (e.g., a web API) can be configured to enable access to the system 150 or outputs thereof by a human agent 240 (e.g., operator or administrator) via portal (e.g., through the presentation of, for example, a care manager dashboard). The REST API 112 can be configured to receive, process, and return requests from an agent device 180 (see FIG. 1B). The computing device 150 may be configured to process information from an agent device 180 in a different manner than through a REST API 112.

In some embodiments, an agent or operator may also access the computing device 150 by means of a telephone. In some embodiments, an agent or operator may also access the computing device 150 by means of a streaming API 108. In some embodiments, a user may access the computing device 150 by means of a REST API 112. In some embodiments, the agents, users, operators, or other parties may access the computing device 150 by means of other modalities.

The AI Care Manager controller 204 can control the AI Care Manager engine 200. For example, it can reformat data into a form acceptable by the AI Care Manager engine 200. The AI Care Manager controller 204 may also provide a means for partners or other external sources to configure the operation of the AI Care Manager engine 200. For example, the AI Care Manager controller 204 may facilitate the entry of external data (e.g., specific protocols, background information or other metadata) into the AI Care Manager engine 200. The AI Care Manager controller 204 may also be configured to route data coming from the AI Care Manager engine 200.

The uploader 116 can be configured to upload configuration data from, for example, an external server 114. In some embodiments, the uploader 116 may form part of the network interface 158. In some embodiments, the system 100 may be reconfigurable based on data for a particular application (e.g., the configuration data). The particular configuration data can be uploaded into the computing device 150 and the models and systems therein can be updated based on the configuration data to provide an AI Care Manager engine 200 capable of carrying out specific conversations. For example, the configuration data may include information regarding a medical device and the AI Care Manager engine 200 can be configured to respond to user queries about the device in a conversational manner. In another example, the configuration data may include information on a particular test (e.g., the PHQ-9 and/or the GAD-7) to provide an AI Care Manager engine 200 capable of assessing the user (e.g., the patient) using the test. As another example, the configuration data may include specific follow-up information (e.g., medication regimes, exercise regimes, discharge instructions, etc.) for a chronic condition monitoring or post-operative condition follow up and the AI Care Manager engine 200 can follow-up with the patient. In some embodiments, the AI Care Manager engine 200 is configured with a wide array of configuration information and is capable of carrying out multiple conversational objectives with the user (e.g., the patient) in a natural and/or conversational fashion. For example, the configuration data may include elements of a patient's profile in the prevailing runtime context. Some of this profile data may be used to deliver a more personalized result in order to increase patient engagement and to drive better outcomes.

In some embodiments, the external server 114 may be an electronic health record database and the data received therefrom may relate to the patient's EHR data. In some embodiments, the external server 114 may include, for example, a payor server. In such embodiments, the configuration data may aid the system in responding to questions about their insurance coverage. In some embodiments, the EHR data can be used to increase the personalization of the system to the user.

The AI Care Manager engine 200 can be configured with a response-generating AI 214 made up of knowledge base or vector database 216 (which may include graph knowledge bases) and a configurable large language model (LLM) 222 (which may be medical LLMs) and configured to receive, interpret, and respond to conversational data (e.g., speech, text, video, etc.) according to a particular script or set of information to be delivered to the user (e.g., the patient) in a natural or conversational manner. The AI Care Manager engine 200 is described in greater detail below, with reference to FIG. 2.

The following discussion refers primarily to LLMs in the context of LLM 222. The LLM 222 is intended to mean a foundational model of which a large-language model is a type. In some embodiments, the LLM 222 may instead be a multimodal (e.g., which can process multiple types of data such as text, images, video, and audio simultaneously). In some embodiments, the LLM 222 may instead be a world model (e.g., which can also process multiple types of data simultaneously).

The sensing engine 117 can be configured to assess the user's conversation with the AI Care Manager engine 200 (or a human agent 240) to assess the user using other sensing modalities. For example the sensing engine may detect the presence, absence, or severity of a health condition (e.g., a physical or mental or behavioural health condition) and/or a state of the user (e.g., confusion, fluency in language, slowness in speech, etc.). In some embodiments, the sensing engine 117 may use audio data. In some embodiments, the sensing engine 117 may use video data (or other sensing modalities) from the conversation to make the determination.

In some embodiments, the sensing engine 117 can receive data from other modalities such as data from wearable devices, data from phone sensors, video information, etc. In some embodiments, the sensing engine 117 may be configured to fuse data from different modalities to generate an output. In some embodiments, the output may be a prediction or assessment of the user. In some embodiments, the output may be features extracted from the sensing modalities. In some embodiments, the output may be fused features or fused data.

In some embodiments, the sensing engine 117 may be a video (or visual) engine configured to process captured images, image streams, etc. to determine bio-signals about the user. This may be used to assess a user state (e.g., assessing the user for fidgeting to determine engagement). A video-based engine may also be used for specific implementations to visually assess the user (e.g., to assess a condition on the user such as an infection or tissue recovery). Such an implementation may make use of an image processing engine configured to extract features from captured images. These features may be used to produce an output that is delivered to the AI Care Manager engine 200 (e.g., it may deliver an assessment of tissue recovery and the AI Care Manager engine 200 may then delivery those results to the user in a response). This is described in greater detail below.

The vocal biomarker engine 118 can be configured to assess the user's conversation with the AI Care Manager engine 200 (or a human agent 240) to detect the presence, absence, or severity of a health condition (e.g., a physical or mental or behavioural health condition) and/or a state of the user (e.g., confusion, fluency in language, slowness in speech, etc.). In some embodiments, the vocal biomarker engine 118 may use acoustic and language data from the conversation to make the determination. In some embodiments, the vocal biomarker engine 118 may also use video data of the user (or video may be processed by, for example, sensing engine 117). The vocal biomarker engine 118 is described in greater detail below, with reference to FIG. 3. The vocal biomarker engine 118 may be a subset of or in communication with the sensing engine 117.

In some embodiments, the outputs from various models can be fused. For example, the output from the vocal biomarker engine 118 may be combined with the output from the sensing engine 117. In some embodiments, the outputs from various models can be combined for joint-modeling.

Storage 120 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM), cloud storage, or the like. The storage 120 may include a database 122 to handle queries and a cloud storage 128 to store one or more of user data 124, clinical/task data 126, media and sensory files 130.

User data 124 may include various user profiles for, for example, patients, caregivers, family members of the patient, human agents 240, and administrators. User data 124 may include an identifier and a status indicator (patient, agent/operator, administrator, etc.) which may control the access for that user. Patient data may include the patient's medical history (or information to access said information through an external server), records of previous conversations, patient metadata (e.g., demographic data or other data which may impact how the AI Care Manager handles the conversation (e.g., if the patient is deaf, then the system may be configured to present information to the user via video or text, i.e., not speech), embeddings of the patients profile, their conversations or parts of conversations). User data 124 may include user preferences and personalizations that are used to tailor their conversations or the generated reply from the AI Care Manager engine 200. The human agents 240 data may include information for each of the patients that the human agents 240 is responsible for and/or information about those patients (e.g., it may provide all information about the patient or it may provide a level of access to patient data for the agent/operator to carry out their duties). The administrator data may include information on all the human agents 240 and or other system usage metrics. For example, the administrators may be able to see the length and success of conversations with particular human agents 240. In some embodiments, the system may be configured to passively listen to agent/operator conversations with the patients and may provide feedback or other key performance indicators regarding the human agents' 240 performance. This data may be used by the administrator to help improve struggling human agents 240. In some embodiments, the system may be configured to provide automatic feedback to the agents using the response-generating AI 214, to evaluate their responses and suggest questions to ask. In some embodiments, the system may be configured to automatically update the AI Care Manager engine 200 using the response-generating AI 214, to improve the system over time (e.g., via established benchmarks, evaluation, etc.).

In some embodiments, the systems and methods described herein can learn from past uses to set preferences on current and future uses. For example, the system can ascertain what communication settings (e.g., speed of responses, complexity of language used, etc.) work best with the user from a previous conversation and implement those settings for future conversations (e.g., within the user data 124).

In some embodiments, the care team (or other parties) may constrain certain patient preferences. For example, while it may be easier for a patient to receive communication one way, it may be better for their long-term recovery to receive information in a different way. For example, while the patient may prefer plain language, it may at times be necessary to nonetheless provide information using longer and more complex communications (e.g., disclaimers). In some embodiments, the patient can set their own preferences. In some embodiments, the patient will have a bounded set of options.

In some embodiments, the care team (or other parties) may set their own preferences that differ from those of the patient (e.g., when delivering information to a human agent, the human agent may prefer to receive more or less detail before initiating a call with a patient). In some embodiments, the care team (or other parties) may be able to configure to system to show them the outputs based on the patient's preferences so that the care team can observe the experience that the patient is receiving. This may be done live or this may be done as an on-demand replay.

In some embodiments, the preferences and/or personalizations may be generated in a global fashion (e.g., based on patient demographics, social determinants of health, or other metadata). This may produce better patient experiences even in initial conversations as the system may deliver information in a manner more likely to be well received by the patient.

In some embodiments, these preferences and/or personalizations may be contextual. For example, they can be time-related (e.g., time of year, time of day, day of week, weekday/weekend) to better meet the patient where they are in their day/week/month/year. The preferences and/or personalizations may be contextually dependent on the patient's health context (e.g. known disability that limits effective use of modality-could be temporary, chronic, permanent, etc.). In some embodiments, the system may be configured to capture the patient's environment and adjust the delivery of information based thereon. For example the system may be able to adapt to, for example, background noise, distractions, other voices, etc.

In some embodiments, the preferences and/or personalizations may vary over time. For example, the system may use more sophisticated language as a child matures into an adult. As another example, the system may adjust the delivery of information based on the patient's changing demographic and health circumstances (e.g., based on their available resources as they age).

In some embodiments, the system may be configured to adjust the delivery of information in real-time (e.g. recognition of events external to current conversation that necessarily change the conversation; e.g., lab results posted, appointment confirmed, like a 911 call, etc.). This may enable the system to deliver timely information or intervention for the patient based on evolving circumstances. For example, in an emergency situation the operator can stay on the line with the caller while situation-relevant resources are called to the scene (parallel work in service of caller/patient).

In some embodiments, the preferences and/or personalizations may be modality based. For example, the preferences and/or personalizations may be applied based on the type of communication modality used (e.g., speech, video, text, etc.). For example, a patient may be more capable of understanding written responses than they are at interpreting verbal responses and consequently, the textual responses may generally include a greater complexity of language.

In some embodiments, the patient may be able to provide the system with communication preferences. For example, the patient may be able to configure the system to reach out using a series of methods of contacts (e.g., call the patient, then text them if the call fails). The patient may also be able to configure the voice that delivers information (in embodiments that make use of speech response). The patient may be able to personalize, for example, the speed, pauses, volume, emotionality, accent (e.g. British English vs Southern American vs. SoCal, etc.), age (older/younger-sounding), gender, vocabulary (e.g., aligned with patient age and education).

In some embodiments, the system may take into account a patient's disability when providing information to the user. For example, the system may make use of visual aids (e.g. closed captioning (video), overlaid images (video), etc.) for hearing-impaired patients or use of high contrast text and images for visually-impaired patients (e.g., color blindness). As another example, the system may make use of audio aids (e.g. avoiding a text-only scenario for visually-impaired patients).

In some embodiments, the system may be configured to adapt the delivery of information to the patient. For example, the system may adapt the way that it summarizes information for the patient or adapt the language in which information is delivered. In some embodiments, the system may include code switching languages. In some embodiments, the system may deliver both text and speech. In some embodiments, the system may be configured to provide information with and without video (and adapt the delivery of content based thereon). In some embodiments, the system can implement closed captioning (e.g., with personalizations for language, font, size, etc.).

Clinical/Task data 126 may include clinical information or task information. For example, it may include information regarding clinical protocols which the system 100 may be configured to order. In that example, the system 100 may identify that the patient should receive a particular clinical test, the system 100 may access clinical/task data 126 to order the clinical test and/or provide information to the patient about the test. In some embodiments, the task information may include information regarding other tasks that the system 100 is configured to carry out. For example, the system 100 may be configured to provide information and access to meal services for patients that suffer food insecurity. As another example, the system 100 may be configured to provide information about transportation services to assist a patient in getting to their appointments. As another example, the system 100 may be configured to assist the patient and healthcare team in executing a care pathway or clinical protocol (e.g., care management coordinated with other systems involved in the overall care of the patient). For example, the AI Care Manager engine 200 may publish particular events to other systems that choose to subscribe to those events in order to take further action or to reflect more complete, current statuses concerning the patient.

Media and sensory files 130 may store the logs of the conversations (e.g., audio logs and/or video logs). This may be beneficial to review conversations between the patients and the AI Care Manager engine 200 to determine the efficacy of the AI Care Manager engine 200 (e.g., as a part of routine reviews). Conversations between human agents 240 may also be recorded to review the efficacy of the human agents 240. The media and sensory files 130 may include the raw audio data of the conversations, video footage of the conversations, transcripts of the conversations, translations of the conversations, computational embeddings of conversation. In some embodiments, the media and sensory files 130 can be used by the AI Care Manager engine 200 to preload the conversation with prior information about the patient.

Each I/O interface 156 enables computing device 150 to interconnect with one or more input devices, such as a keyboard, mouse, camera, touch screen and a microphone, or with one or more output devices such as a display screen and a speaker.

Each network interface 158 enables computing device 150 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switched telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

FIG. 1B shows another example system architecture 101 implementing an AI Care Manager engine 200, according to some embodiments.

The system 101 generally shares many of the same components as system 100. Description regarding system 100 is generally applicable to system 101 and vice versa unless context would dictate otherwise. The system 101 additionally includes a telephone 160, a live web conversation 165, a user device 170, a pre-recorded call 175, an agent device 180, and a network 192.

The telephone 160 may be any form of telephony that may be used by a user (e.g., a patient) to access the computing device 150. The telephone data may be processed using the SIP/VoIP engine 104 to enable telephony over the internet and transferred to the computing device 150.

The live web conversation 165 may be computer device configured to access, for example, the internet and orchestrate a conversation through live web services.

The user device 170 may be a network appliance, embedded device, computer expansion module, personal computer, laptop, personal data assistant, cellular telephone, smartphone device, UMPC tablets, video display terminal, gaming console, electronic reading device, and wireless hypermedia device or any other computing device capable of being configured to carry out the methods described herein. The user device 170 may include a processor 172, memory (not shown), an I/O interface (not shown), and a network interface (not shown).

Each processor 172 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. The processor 172 may be configured to run an app 174 configured to provide the user with access to the computing device 150 by, for example connecting the API 113. The app 174 may transmit and receive information from the computing device 150 to drive a patient conversation with a human agent 240 or an AI Care Manager engine 200 according to methods described herein.

Memory may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. The memory may store the instructions for executing the app 174. The memory may further store patient information thereon.

Each I/O interface enables computing devices to interconnect with one or more input devices, such as a keyboard, mouse, camera, touch screen and a microphone, or with one or more output devices such as a display screen and a speaker. The I/O interface may be configured to receive inputs from the patient (e.g., their conversational information) to transmit it to the computing device 150 and to receive conversational information from an agent 240 or the AI Care Manager engine 200 to present to the patient (e.g., audio, text, video, etc.).

Each network interface enables the user device 170 to communicate with other components, to exchange data with other components, to access and connect to network resources, to serve applications, and perform other computing applications by connecting to a network 192 (or multiple networks) capable of carrying data including the Internet, Ethernet, plain old telephone service (POTS) line, public switched telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. The network interface may interface with network 192 to send and receive information from other components of the system 101 such as the computing device 150.

The pre-recorded calls 175 can be configured to orchestrate pre-recorded calls.

The agent device 180 may be a network appliance, embedded device, computer expansion module, personal computer, laptop, personal data assistant, cellular telephone, smartphone device, UMPC tablets, video display terminal, gaming console, electronic reading device, and wireless hypermedia device or any other computing device capable of being configured to carry out the methods described herein. The agent device 180 may include a processor 182, memory (not shown), an I/O interface (not shown), and a network interface (not shown).

Each processor 182 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. The processor 182 may be configured to run an app 184 configured to provide a human agent 240 with access to the information computed or stored by device 150 by, for example, connecting the API 113. The app 184 may transmit and receive information from the computing device 150 and display it to the human agent 240 with context according to methods described herein. For example, the computing device 150 may redirect a patient to a human agent 240 where the AI Care Manager engine 200 fails to provide a responsive conversation to the patient. In such embodiments, the app 184 may present details of the reasons that the AI Care Manager engine 200 could not run the conversation (e.g., difficulty in understanding the patient). The app 184 may display an overview and statistics of calls, assessments done by vocal biomarker engine, suggestion of next questions for an agent to ask, etc.

Memory may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. The memory may store the instructions for executing the app 184. The memory may further store agent information thereon.

Each I/O interface enables the agent device 180 to interconnect with one or more input devices, such as a keyboard, mouse, camera, touch screen and a microphone, or with one or more output devices such as a display screen and a speaker.

Each network interface enables the agent device 180 to communicate with other components, to exchange data with other components, to access and connect to network resources, to serve applications, and perform other computing applications by connecting to a network 192 (or multiple networks) capable of carrying data including the Internet, Ethernet, plain old telephone service (POTS) line, public switched telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. The network interface may interface with network 192 to send and receive information from other components of the system 101 such as the computing device 150.

The external server 114 may be any external source of additional information. There may be multiple external servers 114 each providing redundant or dissimilar information. In some embodiments, the external server 114 may provide, for example, configuration data. The external server 114 may also update the system with the outcome of any conversations taken care of with the system 101. In some embodiments, the external server 114 may be a server containing electronic health records (EHRs). In some embodiments, the external server 114 can be a payor server configured to provide the AI Care Manager engine 200 with information about, for example, the patient's insurance coverage.

The network 192 may be a network (or multiple networks) capable of carrying data including the Internet, Ethernet, plain old telephone service (POTS) line, public switched telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. The network 192 may connect one or more of the computing devices 150, the telephone 160, the user device 170, the agent device 180, and the external server(s) 114.

The computing device 150 may further include APIs 113 and a process engine 119. The network interface 158 may include the APIs 113 (e.g., e.g., streaming API 108 and REST API 112) that may enable communication between different components of the system. The process engine 119 may be configured to handle and follow-up tasks identified during the course of a conversation with the AI Care Manager engine 200 (or a human agent 240). The process engine 119 can generate and action administrative or clinical tasks based on the patient interview through a real-time natural conversation with a patient in service to the healthcare team. The process engine 119 when linked to the AI Care Manager engine 200 can identify tasks and requests generated through the conversation and automates any processes for the clinical team through direct interface with the EHR or other platforms the healthcare team uses when caring for the patient.

In operation, the systems 100 and 101 operate to drive a conversation between a patient and an AI Care Manager engine 200. The patient can choose to engage with the system 100 or 101 using, for example, a phone conversation or an app-based conversation. If the patient uses a phone conversation then they may use a telephone 160 to call, for example, a dedicated number that directs the patient to the computing device 150. The SIP/VoIP engine 104 may facilitate the provision of telephony for the patient. If the patient uses an app-based conversation, then they may use a user device 170 to access, for example, an app 174 that can access the computing device 150. The app 174 may use APIs 113 to access, send and receive information from the computing device 150. The app 174 may alternatively use a different computer architecture to send and receive information from the computing device 150.

The patient can connect to the computing device 150 and the computing device 150 can provide the patient with access to the AI Care Manager engine 200 (which is described in greater detail below). In some embodiments, the conversation is initiated by the patient (e.g., the patient calls in for clarification on their prescriptions). Put another way, the patient can call the AI Care Manager engine 200 to discuss whatever the patient wants. In such embodiments, the AI Care Manager engine 200 may be configured to ask open-ended questions to provoke targeted questions from the patient that the AI Care Manager engine 200 can then answer (e.g., "What seems to be the problem today?" or "What did you want to talk about?") or the user may be able to quickly direct the conversation (e.g., the AI Care Manager engine 200 lets the patient take the conversational lead initially). In some embodiments, the conversation is initiated (or otherwise previously scheduled) by the AI Care Manager engine 200. In such embodiments, the AI Care Manager engine 200 may have specific items which it will work through with the patient (e.g., may have to get information on how the patient's recovery from surgery is going).

In some embodiments, the system may be configured to receive inbound patient calls. In some embodiments, the system may be configured to assess the inbound calls to decide if the call continues. For example, the system may be configured to ascertain the topic of the user's call and determine whether the topic is one that the system can respond to. In some embodiments, the system may carry out patient eligibility confirmation. In some embodiments, suitable inbound calls may include patients asking to enroll in a program or adding or changing information from a past or current conversation. In some embodiments, the inbound calls may undertake patient verification to ensure that they are addressing the correct patient or other compliance requirements (e.g., automated disclosures) before, for example, handing the patient off to a human agent 240.

During the conversation, the AI Care Manager engine 200 may generate and action various tasks. For example, if the patient mentions being hungry, then the AI Care Manager engine 200 may be configured to inquire as to the reasons. The AI Care Manager engine 200 may then provide the patient with resources on a food program should the hunger be caused by food insecurity. The AI Care Manager engine 200 may be configured to reach out to such programs on the patient's behalf (e.g., using process engine 119). As another example, if the patient runs out of a specific medicine, then the AI Care Manager engine 200 may be configured to request a refill from a local pharmacy (e.g., using process engine 119).

The AI Care Manager engine 200 may be configured to access information about the patient and/or protocols prior to the start of the conversation. The AI Care Manager engine 200 may operate by receiving the conversational data from the patient, analyzing the conversational data, and generating a response to the conversational data which is then delivered to the patient. In some embodiments, the response may be transmitted a third party instead of the patient (e.g., to a physician).

Optionally, the system 100 or 101 may include a sensing engine 117. The sensing engine 117 may be configured to observe the conversation using other input modalities (e.g., video) and assess the patient based on the other inputs. The sensing engine 117 may determine the presence, severity, and/or absence of specific conditions. The sensing engine 117 may provide its determination as a report. The report may be provided to a human agent 240 or to another member of the healthcare team if certain conditions are met or it may be saved to the patient's file and/or to their EHR. The sensing engine 117 may further be configured to provide its determination to the AI Care Manager engine 200 which may then use this information to inform the conversation that the AI Care Manager engine 200 is conducting with the patient. For example, the sensing engine 117 may for example use the video data of the patient to assess the patient's candour or confidence in what they are saying. If the sensing engine 117 detects that the patient may not be confident in what they are saying, then the sensing engine 117 may prompt the AI Care Manager engine 200 to further inquire regarding the patient's last response.

In some embodiments, the sensing engine 117 can receive data from other modalities such as data from wearable devices, data from phone sensors, video information, etc. In some embodiments, the sensing engine 117 may be configured to fuse data from different modalities to generate an output. In some embodiments, the output may be a prediction or assessment of the user. In some embodiments, the output may be features extracted from the sensing modalities. In some embodiments, the output may be fused features or fused data.

Optionally, the system 100 or 101 may include a vocal biomarker engine 118 (which may be a subset of the sensing engine 117; described in greater detail below). The vocal biomarker engine 118 may be configured to listen to the conversation and assess the patient based on the conversational data. The vocal biomarker engine 118 may determine the presence, severity, and/or absence of specific conditions. The vocal biomarker engine 118 may provide its determination as a report. The report may be provided to a human agent 240 or to another member of the healthcare team if certain conditions are met or it may be saved to the patient's file and/or to their EHR. The vocal biomarker engine 118 may further be configured to provide its determination to the AI Care Mana ger engine 200 which may then use this information to inform the conversation that the AI Care Manager engine 200 is conducting with the patient. For example, if there is a determination that the patient may be depressed, then the AI Care Manager engine 200 may begin to ask questions to increase the certainty of that determination or the AI Care Manager engine 200 may provide the patient with additional resources for depression or schedule a follow up appointment with the appropriate physician. The vocal biomarker engine 118 may also detect fluency of the patient in the language used, patient boredom, slowness in speech, patient confusion, etc. The system 100 or 101 may use these metrics to modify the direction of the conversation. For example, the system 100 or 101 may change the language if it detects that the patient is not sufficiently fluent in the current language, may present the content more quickly if it determines the patient is bored, it may slow the presentation of content if it determines the patient is speaking slowly. The system 100 or 101 may also go back over things if it determines that the patient does not understand the content (e.g., confusion).

The system 100 or 101 may also include a process engine 119. The process engine 119 may be configured to generate and action clinical and/or administrative tasks based on the conversation with the AI Care Manager engine 200. For example, if the AI Care Manager engine 200 determines that the patient needs a refill on one of their prescriptions, the process engine 119 may be configured to generate and action that task, for example, by interfacing with the pharmacy system to place a refill order. The process engine 119 may be a collection of interfaces to act on tasks with many different external systems.

Figure 2:
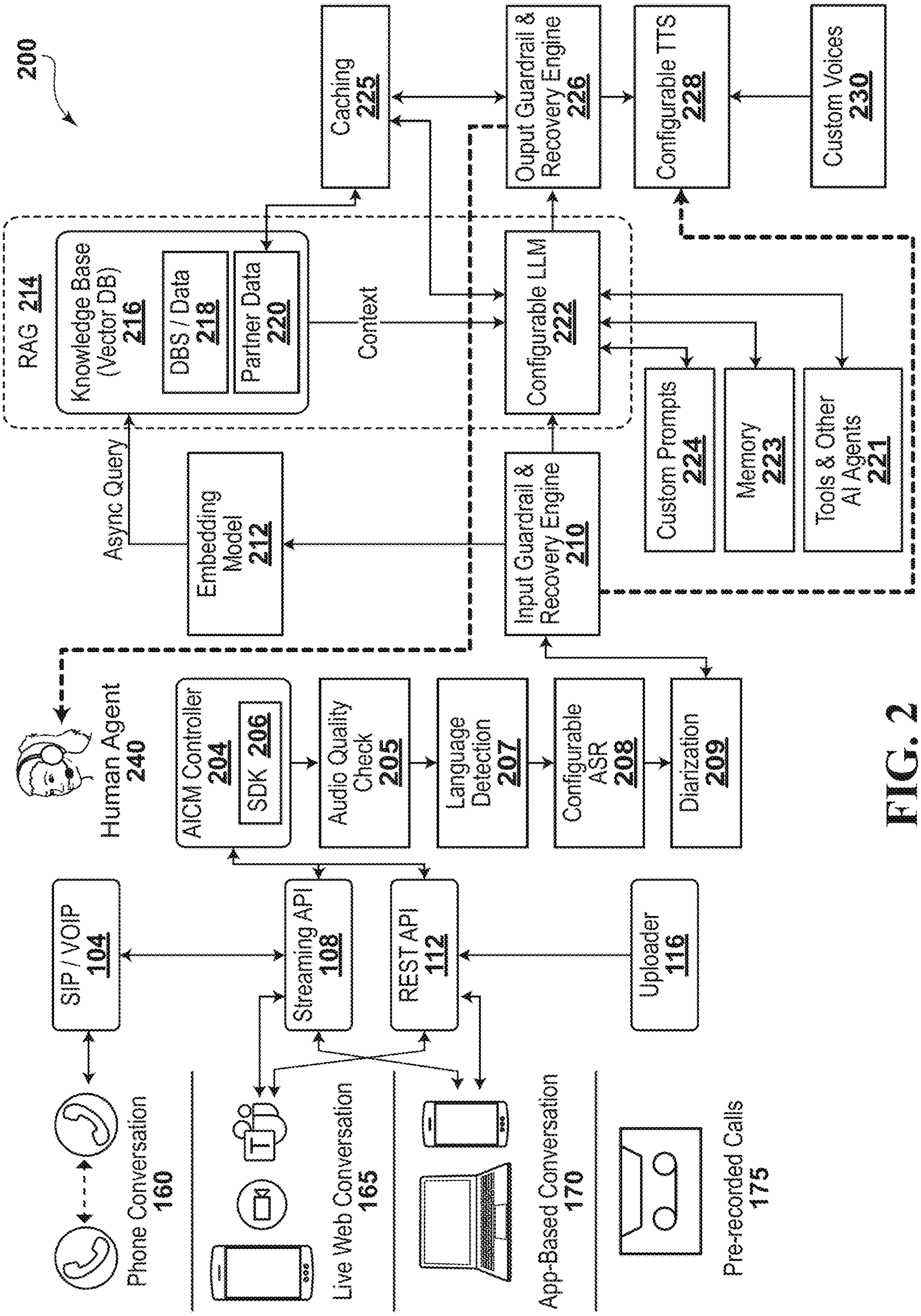
FIG. 2 shows an example architecture for the AI care manager, according to some embodiments.

FIG. 2 shows an example architecture for the AI Care Manager engine 200, according to some embodiments.

The AI Care Manager engine 200 includes an input guardrail 210, an embedding model 212, a response-generating AI 214, a cache 225, and an output guardrail 226. In circumstances where the AI Care Manager engine 200 is configured to receive and generate speech data as the conversational data, the AI Care Manager engine 200 may further include an audio quality check 205, a language detection 207, an automatic speech recognition engine 208, diarization 209, and a text-to-speech engine 228. The AI Care Manager engine 200 may further include custom prompts 224, custom voices 230, memory 223, and tools and other AI agents 221. The AI Care Manager engine 200 may also include a module that redirects calls to a human agent 240. The AI Care Manager engine 200 may also include components that can extract audio from video call services (e.g., Zoom or other such services).

In some embodiments, the systems described herein are configured to carry out dynamic call scheduling based on the availability of the patient (based on, for example, their preferences, normal working hours in their time zone, day of the week, etc.). In some embodiments, the systems described herein are configured to carry out dynamic call scheduling based on the availability of the agents (e.g., based on the agents'working hours, the time zone, the day of the week, etc.). The systems described herein may redirect calls to human agents 240 based on their availability. The systems described herein may enable an operator (or other member of a care team) to develop conversational objectives and tasks associated therewith. These may be based on patient cohorts (e.g., based on patient demographics or other shared attributes). The operator may push those conversational objectives and tasks to the patients and the systems described herein may schedule calls with the patients dynamically in a manner that optimized the effectiveness and efficiency over the least amount of time necessary. The systems described herein may also be configured to provide status updates based on ongoing progress.

Before the conversation begins, the response-generating AI 214 may be pre-loaded with patient-specific information. For example, the response-generating AI 214 may be provided with information about the patient's medical history, patient preferences (e.g., does the patient require the AI Care Manager engine 200 to provide information at a slow pace, does the patient need things explained simply due to, for example, cognitive impairment, etc.), prior conversations with the patient, and/or general instructions to the system. This information can be loaded using the custom prompts 224 and/or from the knowledge base 216.

In modalities wherein the conversational data is received as speech, the automatic speech recognition engine 208 can transcribe the input speech (e.g., conversational data) provided to the system into textual form. The automatic speech recognition engine 208 can use any program configured to convert speech to text. In some embodiments, the input conversational data is already in textual form (e.g., if the user is typing their queries into an app and those are being submitted as a text-message) and the automatic speech recognition engine 208 is not needed. In some embodiments, the AI Care Manager engine 200 is configured to operate using different modes of input (e.g., operating directly off of speech data). In some embodiments, the AI Care Manager engine 200 may have multiple transcription systems available to the automatic speech recognition engine 208. For example, the automatic speech recognition engine 208 may be configured to identify speech in one language and transcribe it into a different language (e.g., the language of the response-generating AI 214). In some embodiments, the AI Care Manager engine 200 may pass the transcribed speech from the automatic speech recognition engine 208 to other components of the system such as the vocal biomarker engine 118 and the sensing engine 117 (to the extent such components are present in the system 100 or 101).

In some embodiments, the AI Care Manager engine 200 may be configured to translate the input conversational data into another language (e.g., the language of the response-generating AI 214). This may be beneficial to ensure that the input guardrail 210, the response-generating AI 214, or the output guardrail 226 can operate in the language with which they were trained. In some embodiments, the system may be configured to deliver output responses in text. In such embodiments, the system may be configured to generate output responses by writing them out in different languages.

In an example implementation, a patient's conversational data may be directed through pre-processing before being delivered to the response-generating AI 214. For example, the AICM controller 204 may transmit the conversational data to an audio quality check 205. The audio quality check 205 may confirm that the conversational data is of sufficient quality to be reliably processed by the system. This can provide a preliminary and robust assessment to prevent poor quality data from reaching the response-generating AI 214 which can help reduce or eliminate hallucination. If the conversational data does not pass the audio quality check 205, then it may not be transmitted further in the system. Optionally, remedial actions may be taken (e.g., the system may ask the patient to fix their audio settings). If the audio quality check 205 passes, then the conversational data may then be transmitted to the language detection 207. The language detection 207 may detect the language in the conversational data. The detected language may be used to configure how the AI Care manager 200 will operate. For example, models trained with the detected language may be selected for the ASR 208, the input guardrail 210, the response-generating AI 214, the embedding model 212, the cache 225, the output guardrail 226, and/or the TTS 228, etc. Alternatively, or additionally, if the detected language differs from the model languages, then the conversation data may be translated (at some point in processing, e.g., the ASR 208 may transcribe the speech in the detected language and the transcribed speech may then be translated) into the model languages. The ASR 208 may then transcribe the speech data into transcribed conversational data. Finally, before the transcribed conversational data is provided to the input guardrail 210, diarization 209 may diarize the transcribed conversational data. Diarization 209 may be effective to provide a summary of the conversation.

The input guardrail 210 may provide a check for the validity of the transcribed input conversational data. For example, the input guardrail 210 may check the input statement to determine whether it can be understood (e.g., if the patient spoke clearly or the automatic speech recognition engine 208 transcribed the speech correctly). The input guardrail 210 can also assess the conversation to determine whether there are inappropriate expressions (e.g., expletives used, or the patient is speaking to the AI Care Manager engine 200 in an improper manner (e.g., flirting with the AI Care Manager engine 200)). The input guardrail 210 may check for inappropriate conversation because admitting such conversation to the response-generating AI 214 may generate inappropriate responses (e.g., hallucinations). In some embodiments, the input guardrail 210 may also detect inappropriate topics. In such embodiments, the topic may be ones on which an AI Care Manager engine 200 is not qualified to provide feedback to the patient (e.g., questions regarding prescribing medicine).

In some embodiments, the input guardrail 210 may be configured to redirect the conversation to a human agent 240 if the input guardrail 210 classifies the conversational data as bad (e.g., the conversational data includes data that is one or more of unintelligible, exhibits inappropriate behaviour, or inappropriate topics). The input guardrail 210 may be configured to bypass the standard processing method and direct the AI Care Manager engine 200 to attempt to remedy the issue. For example, if there was a failure to understand or transcribe the conversation, then the AI Care Manager engine 200 may ask the patient to repeat or clarify their previous response. As another example, if the patient is using inappropriate behaviour towards the AI Care Manager engine 200, then the AI Care Manager engine 200 may clarify for the patient that it is a computer generated agent. As another example, if the patient asks the AI Care Manager engine 200 to prescribe it medicine, then the AI Care Manager engine 200 may redirect the patient to a physician (e.g., schedule an appointment using process engine 119), tell the patient that it does not have the ability to prescribe anything, and continue the conversation.

The purpose of the input guardrail 210 is to ensure that proper and expected input conversational data (e.g., transcribed speech data) is provided to the response-generating AI 214 and to redirect the patient should that be determined the best course of action. This can ensure that the patient is processed by the system efficiently (e.g., escalating patients to a human agent 240 where the response-generating AI 214 may struggle to process and respond). It also reduces the amount of improper data that is processed by the response-generating AI 214 which increases the processing efficiency of the AI Care Manager engine 200 and the accuracy of the responses.

The input guardrail 210 may be a model that is configured to classify the conversational data as bad where it meets one or more criteria (e.g., unintelligibility, inappropriate behaviour, or inappropriate topic). For example, the input guardrail 210 might be a rules-based or machine learning model that is configured to assess the conversational data (e.g., output from the automatic speech recognition engine 208). The input guardrail 210 may also be a smaller LLM capable of determining whether the input conversational data provided makes sense based on the flow of the conversation. The input guardrail 210 may also be some combination of rules-based, machine learning model, and LLM. The input guardrail 210 can be configured such that it can process the conversational data quickly.

If the conversational data clears the input guardrail 210 (e.g., it is classified as good), then it is provided to the embedding model 212. The embedding model 212 can embed the conversational data into feature space. In some embodiments, other methods can be used. In some embodiments, the embedding model 212 can embed the conversational data as well as all prior context (e.g., the prior conversation, any patient information, pre-loaded information, general instructions, etc.). In some embodiments, the system 100 and/or 101 can cache or otherwise save information after it has been embedded by embedding model 212 or model 222 (e.g., with caching 225). This can reduce the time for embeddings because only new information needs to be embedded. This may make the AI Care Manager engine 200 able to respond more quickly to patient questions. This may also make it more feasible for the system to receive and process complex inputs made up of lengthy patient interviews, general instructions, information on past sessions, health information, etc.

In some embodiments, the conversational data may bypass the knowledge base 216 and be sent directly to the response-generating AI 214 (e.g., the LLM 222). In such embodiments, the conversational data may be embedded directly by the response-generating AI 214 rather than by the embedding model 212. In some embodiments, conversational data may be routed based on its content (e.g., if it is classified as bad by the input guardrail 210, it may be routed through the response-generating AI 214 to generate a responsive reply that indicates an error).

In some embodiments, for example when the input guardrail 210 is triggered, the AI Care Manager engine 200 may be configured to prepare the user for a transfer to a human agent 240. For example, the AI Care Manager engine 200 may use the trigger to determine the context of the redirection and may explain that is why the call is being redirected. For example, in a simple case, if the user requests that the call be redirected to a human agent 240 than the AI Care Manager engine 200 may be configured to simply state that the user is being transferred because they have requested it. They AI Care Manager engine 200 may also provide an expected wait time. This may also give the user the opportunity to rescind their request and continue with AI Care Manager engine 200. As another example, if the user repeatedly makes inappropriate requests of the AI Care Manager engine 200 and even after attempted remediation the user continues to make these requested, then the AI Care Manager engine 200 may be configured to explain to the user that the topics of the user's requests are outside its scope and so it is redirecting the user to a human agent 240 who may be better equipped to handle the user (or the AI Care Manager engine 200 may redirect the user to, for example, a physician who is qualified to speak on the topics).

In some embodiments, the input guardrail 210 may also be configured to determine the response time and the input guardrail 210 may throw a trigger if too much time has elapsed. For example, after the AI Care Manager engine 200 delivers its response, then the input guardrail 210 may be configured to start timing how long the AI Care Manager engine 200 has waited. After a period of time, the input guardrail 210 may follow up response to the user to see if they are still present (e.g., "what do you think about" [recitation of previous response]). In some embodiments, the input guardrail 210 may determine that the user has left the conversation and terminate the session. This might be important in conversational modalities without defined endings (e.g., text-based conversations where the user may simply stop replying). Ending the conversations in a timely manner can free up system resources to orchestrate other conversations with other users. This can reduce the overall cost of the system and provide users with timelier service.

In some embodiments, the timing of when a follow up response is generated can be pre-defined. In some embodiments, the timing of when a follow up response is generated can be based on the conversational modality (e.g., the norms for response times may be longer for texting). In some embodiments, the timing of when a follow up response is generated can be based on the conversation itself (e.g., the AI Care Manager engine 200 may tolerate slightly longer delays when the user seems engaged in the conversation and likely to reply).

In some embodiments, some Personal Health Information (PHI) and Personally Identifiable Information (PII) can be removed before passing the conversational data to the response-generating AI 214. This can prevent some information from being transmitted to the response-generating AI 214 which may help protect the privacy of this information or may be useful to prevent the response-generating AI 214 responses from being influenced by what should be irrelevant information.

In some embodiments, the AI Care Manager engine 200 has been trained with data wherein the PHI and PII has been removed. The removal of the PHI and PII may be useful to train the AI Care Manager engine 200 to assess the conversation itself rather than, for example, pulling an assessment from the PHI.

The response-generating AI 214 may be made up of a knowledge base 216 and a large language model (LLM) 222. The knowledge base 216 may be made up of custom training 218 and optionally configuration data 220. The knowledge base 216 may provide the context (e.g., a collection of files (documents, images, etc.)). The knowledge base 216 can be structured or unstructured. The knowledge database 216 can be a collection of databases and/or knowledge graphs and/or large language models. The configuration data 220 may provide the specific applications of the AI Care Manager engine 200 (e.g., product information, instructions, scripts that the AI Care Manager engine 200 can use to direct conversations, etc.). The custom training 218 may be configured to parse through the configuration data 220 to provide useful information to the response-generating AI 214. In some embodiments, the response-generating AI 214 may be a retrieval-augmented generation AI 214. The response-generating AI 214 may be configured to generate responses with different computational architecture(s) as well.

In some embodiments, the knowledge base 216 can be a vector knowledge base. In some embodiments, the knowledge base 216 can be a graph knowledge base. In some embodiments, the knowledge base 216 may use other computational architectures. The embedding model 212 may be any model configured to transform the input conversational data into the requisite form for interpretation with the knowledge base 216 (e.g., vector, graph, etc.).

Embedded conversational data and context are provided to the LLM 222 for processing. The LLM 222 can take the embedded conversational data and context and generate its reply based thereon. The context allows the LLM 222 to run through certain objectives during the conversation (e.g., conversational objectives) in addition to generating replies that are natural and conversational and remaining responsive to the patient. For example, conversational objectives can include inquiring about specific follow-up questions (e.g., recovery, mobility, medicinal regime adherence, etc.).

The custom prompts 224 can be provided to the response-generating AI 214 (e.g., the LLM 222). These prompts 224 can be configured to elicit helpful responses from the response-generating AI 214. The custom prompts 224 can also be configured to format any background information or prior context for the response-generating AI 214. The custom prompts 224 may also format the incoming data in a manner less likely to produce unhelpful, unresponsive, or harmful outputs (e.g., if the patient asked something in an unusual manner that could be misinterpreted). The custom prompts 224 may originate in collaboration with a third party (e.g., the client). For example, there may be an existing and field-tested script that can serve as the foundation of the custom prompts 224. The custom prompts 224 may be based in part on system learning. For example, subsequent conversations should reflect learnings from prior conversations and improve the AI Care Manager engine 200 to benefit all patients downstream. The AI Care Manager engine 200 can transform scripts (e.g., designed for human beings) into custom prompts 224 that lead to a runtime experience that is human-like from the patient's point of view and in a way that effectively scales to a population or a much larger cohort of similar patients.

Memory 223 may provide the LLM 224 with information stored therein.

In some embodiments the LLM 222 may make use of tools and other AI agents 221. In some embodiments, the outputs of the LLM 222 are provided in structures configured to be interoperable with other AI agents (e.g., a Triage Agent, a Cardiology Agent, a Billing Agent, etc.). The structure may include headers for intent, payload for medical data, and security tokens. This can allow the AI Care Manager engine 200 to interoperate with other agents.

Once the response-generating AI 214 generates a reply, then the reply may also be cached in the cache 225. This may help provide context to the conversation in future conversational turns.

Output guardrail 226 may provide a check for the safety of the generated reply. For example, the output guardrail 226 may check the generated reply to determine whether the generated reply is responsive, correct, and/or not harmful. For example, the output guardrail 226 may conduct a check to ensure that the generated reply is responsive to any patient query or statement. For example, the output guardrail 226 may be configured to check that the information within the generated reply is factually accurate (e.g., as checked against medical information or the patient's medical history). As another example, the output guardrail 226 may check that the generated reply does not include any information or instructions that might be harmful to the patient (e.g., it may check that the generated reply doesn't instruct the patient to take anything to which they are allergic, or it may check that the generated reply does not instruct the patient to undertake an action that would harm the patient or others). In some embodiments, the output guardrail 226 may check to see if the generated reply is related to an inappropriate topic. For example, the output guardrail 226 may check to see if the generated reply recommends a medication and, if so, stops that response from going through.

In some embodiments, the output guardrail 226 may be configured to redirect the conversation to a human agent 240 if the output guardrail 226 classifies the reply as bad. The output guardrail 226 may be configured to bypass the standard processing method and direct the AI Care Manager engine 200 to attempt to remedy the issue. For example, the AI Care Manager engine 200 may rerun the input to the response-generating AI 214 to see if it outputs a different generated reply. The AI Care Manager engine 200 may ask for clarification or may remind the patient that it's a computer generated agent to attempt to elicit a different response from the patient. The AI Care Manager engine 200 may explicitly tell the patient that it's unable to provide information on certain topics (e.g., tell the patient that it cannot recommend medication) and continue the conversation. The AI Care Manager engine 200 may connect the patient with a human agent 240.

The purpose of the output guardrail 226 is to ensure that safe and proper replies are provided to the patient and to redirect the patient should that be determined the best course of action. This can ensure that the patient is processed by the system efficiently (e.g., escalating patients to a human agent 240 where the response-generating AI 214 may struggle to generate an appropriate reply). It also reduces the likelihood that the AI Care Manager engine 200 exceeds its scope of expertise or provides a harmful or non-responsive reply.

The output guardrail 226 may be a model that is configured to classify the reply as bad if it meets one or more criteria (e.g., non-responsive, inaccurate, or harmful). For example, the output guardrail 226 might be a rules-based model that is configured to assess the output from the response-generating AI 214. The output guardrail 226 may also be a smaller LLM capable of determining whether the generated reply provided makes sense based on the flow of the conversation. The output guardrail 226 can be configured such that it can process the conversational data quickly.

In some embodiments, for example when the output guardrail 226 is triggered, the AI Care Manager engine 200 may be configured to prepare the user for a transfer to a human agent 240. For example, the AI Care Manager engine 200 may use the trigger to determine the context of the redirection and may explain that is why the call is being redirected. For example, if the response to the user's query requires medical advice that the AI Care Manager engine 200 is not qualified to deliver, then the AI Care Manager engine 200 may explain that the response to the user's query is outside the scope of its expertise and that the AI Care Manager engine 200 is referring it to a human agent 240 (or a physician) who may be better situated to respond. As another example, if there is a complicated trigger that has arisen over the course of the conversation, then the AI Care Manager engine 200 may explain that it is sorry it cannot help, but that it will redirect the user to a human agent 240 to better assist the user.

In some embodiments, the output guardrail 226 may also be configured to determine the response time and the output guardrail 226 may throw a trigger if too much time has elapsed. For example, after the user finishes an input, then the output guardrail 226 may be configured to start timing how long the user has waited. After a period of time, the output guardrail 226 may generate a response to the user to keep the user engaged (e.g., "thanks so much for your patience, I am still thinking about how to respond"). In some embodiments, the output guardrail 226 may be configured to extract some information from the user's query to personalize the response. In some embodiments, the output guardrail 226 might pull information from the cache 225 to personalize the response. In some embodiments, the nature of the engagement response might be tailored to the conversational modality (for example, for conversations by text, the engagement response may include simply putting a draft response in a text box so the users sees a typing ellipsis for short delays).

In some embodiments, the timing of when a response to keep the user is engaged is generated can be pre-defined. In some embodiments, the timing of when a response to keep the user is engaged is generated can be based on the conversational modality (e.g., the norms for response times may be longer for texting). In some embodiments, the timing of when a response to keep the user is engaged is generated can be based on the conversation itself (e.g., the AI Care Manager engine 200 may tolerate slightly longer delays when the user seems engaged in the conversation, whereas the AI Care Manager engine 200 may make more attempts to keep the user engaged where they do not seem engaged).

In some embodiments, when the patient is redirected to a human agent 240, the human agent 240 may be given a summary of the conversation and/or information regarding why the conversation has been redirected. For example, the human agent 240 may see that this was at the request of the patient or the human agent 240 may see the summary of the guardrail 210, 226 triggers that redirected the conversation. In some embodiments, the summary of the conversation thus far avoid the need for the patient to repeat the information.

In some embodiments, the guardrails 210, 226 are customizable. Accordingly, the system operator can set up behaviour for what will activate the guardrails 210, 226 and how they will react. For example, when triggered, the guardrails 210, 226 may be configurable to either terminate the conversation or to retry, for example, response generation, or to attempt to elicit more information from the user. The system operator may be able to select which of these options the guardrails 210, 226 will undertake when the guardrails 210, 226 is triggered.

In modalities wherein the conversational data is received as speech, the text-to-speech engine 228 may take a generated reply and convert it to, for example, an audio response for the patient. The text-to-speech engine 228 may make use of custom voices 230 to generate speech that is more natural or comfortable for the patient. In some embodiments, there may be no text-to-speech engine 228, for example if the AI Care Manager engine 200 is delivering responses by text (e.g., in a text-message conversation). In such embodiments, the reply may be sent to the patient's device once the generated reply is classified as good by the output guardrail 226.

The AI Care Manager controller 204 may include a software development kit 206. The software development kit 206 may include tools to allow external or internal parties to configure the AI Care Manager engine 200. This may enable external parties to provide configuration information 220 and configure the operation of the AI Care Manager engine 200 to carry out specific functions described herein. The AI Care Manager controller 204 may alternatively be configured with other software means to mediate and configure the AI Care Manager engine 200. The AI Care Manager controller 204 may also route the generated replies back to the patients.

In some embodiments, the system 100 and 101 may be configured to incorporate previous conversations with the patient into its responses. In such embodiments, it may pre-load the response-generating AI 214 with these prior conversations. However, such conversations may be lengthy. Accordingly, in some embodiments, the system 100 and 101 may be configured to produce output summaries of the conversation that can be used for future pre-loading into the response-generating AI 214. These summaries may retain the substance of prior conversations, but may truncate extraneous information and briefly summarize the important information such that the response-generating AI 214 is able to speak intelligently about past conversations without necessarily needing the exact information in the past conversations. These summaries may also be provided to any human agents 240 to give them context about the patient if/when the patient is directed to a human agent 240. In some embodiments, the prior conversations may be split into chunks. For example, the system 100 and 101 may be configured to chunk the prior conversations. It may do so based on topic and then pre-load the response-generating AI 214 with only relevant chunks (e.g., chunks related to topics that are intended to be discussed with the patient in a subsequent conversation). In such embodiments, additional chunks may be fed to the response-generating AI 214 during the conversation (e.g., where the patient brings up a topic that the system 100 and 101 didn't expect to discuss).

In operation, prior to initiating a conversation with the patient, the AI Care Manager engine 200 may pre-load the response-generating AI 214 with any relevant information. For example, the response-generating AI 214 may be pre-loaded with the patient's medical history and any scripts that the AI Care Manager engine 200 can generally follow to retrieve information from the patient in this conversation. In some embodiments, the response-generating AI 214 may be loaded with information from past conversations the patient has had either with the AI Care Manager engine 200 or a human agent 240. In some embodiments, this information may be pre-loaded as the entire conversation or a summary of the same. In some embodiments, this may be input into the response-generating AI 214 by embedding model 212. The embedded pre-loaded information may then be cached such that it need not be embedded by the embedding model 212 thus saving processing resources and time during the conversation. In such embodiments, data may be chunked (e.g., split into parts before or after embedding) and used as such for feeding into the response-generating AI 214.

The patient may provide input conversational data into the response-generating AI 214 that may be passed through the AI Care Manager controller 201 within the AI Care Manager engine 200. The input conversation may be converted from speech to text by the automatic speech recognition engine 208 if the conversational data includes speech. The conversational data may be run through the input guardrail 210 to identify whether the conversational data is intelligible (e.g., transcribed properly, generally comprehensible), includes appropriate behaviour (e.g., not behaving in a manner the AI Care Manager engine 200 is not trained to respond to), and includes appropriate topics (e.g., not asking about a topic that the AI Care Manager engine 200 should not respond to). If the input guardrail 210 classifies the input conversation as bad, then it may try to remedy the situation by immediately bypassing processing by the response generation AI 214 and having the text-to-speech engine 228 (if the output modality is speech) generate and output a clarifying question or clarifying response or by inputting the classification by input guardrail 210 into the response generation AI 214 to generate a clarifying question or clarifying response based on the nature of the conversation input classification by the input guardrail 210. If the clarifying question or response does not fix the issue, or if the AI Care Manager engine 200 deems appropriate, then the AI Care Manager engine 200 may direct the patient to a human agent 240. If the input guardrail 210 classifies the input conversation as good, then the conversational data may be embedded by the embedding model 212 and/or passed to response-generating AI 214.

The embedded conversational data may be provided to the response-generating AI 214 (e.g., the LLM 222) along with any appropriate context from, for example, the custom training 218 and the configuration data 220. This information may be delivered to the response-generating AI 214 which is using custom prompts 224. The configuration data 220 may configure the AI Care Manager engine 200 to inquire about pre-defined topics of interest (or other conversational objectives). The response-generating AI 214 may generate a reply to the patient's input conversational data. The generated reply may be run through the output guardrail 226 to identify whether the reply is responsive (e.g., to any patient queries), accurate (e.g., correct information being delivered), not harmful (e.g., not providing instructions to the patient likely to harm them or others, e.g., allergies), and not on an inappropriate topic (e.g., it does not attempt to prescribe a medication). If any of these are present, then the output guardrail 226 may try to remedy the situation, for example, by asking a clarifying question or making a clarifying statement. It may return the request to response-generating AI 214 with instructions how to produce better response, in which case the response-generating AI 214 will produce the response and send it to output guardrail 226 for another review. Alternatively, or if the remedying attempts fail, the output guardrail 226 might direct the patient to a human agent 240. If the output guardrail 226 classifies the generated reply as good, then the generated reply may be converted to speech using the text-to-speech engine 228 if the conversation modality includes speech. The text-to-speech engine 228 may use custom voices 230 to generate the speech. The audio output reply may then be delivered to the patient using the communication method of the AI Care Manager engine 200 (e.g., audio output to a telephone, audio or textual to an app, etc.). In embodiments that make use of textual modes of communication, the text-to-speech 228 may not be used and the generated reply may be sent directly as a text.

In some embodiments, the AI Care Manager Engine 200 can be configured to detect and respond to different languages. For example, the components of the AI Care Manager engine 200 (e.g., the input guardrail 210, the response-generating AI 214, the output guardrail 226, etc.) may be multilingual. In some embodiments, there may additional components in the AI Care Manager engine 200 configured to translate the inputs and outputs (e.g., the language may be translated from the patient's language to the model language after the automatic speech recognition has been done or translated back from the model languages to the patient's language before text-to-speech). In some embodiments, the components (e.g., the automatic speech recognition 208 and the text-to-speech 228) themselves may be configured to translate the speech. In some embodiments, the AI Care Manager engine 200 may be configured to detect the incoming language and decide what to do based thereon. For example, the system may permit the language through if the models are capable of generating a reply with that language (e.g., multi-lingual and inclusive of the patient's language) or it may decide to translate the input into a model language and the output back to the patient's language. In some embodiments, the AI Care Manager engine 200 may redirect the conversation to a human agent 240 where the language used by the patient does not match the model language.

In some embodiments, the systems described herein may make use of speech-to-speech pipelines. In some embodiments, the speech-to-speech pipelines include a speech-to-text (e.g., automatic speech recognition engine 208) to convert the user speech into textual information, a response-generating AI 214 to generate responses using, for example, a large language model (LLM 222) to generate responses using custom prompts 224, and guardrails 210 and 226, and a text-to-speech model 228 that is configured to convert the generated reply into speech for the user.

In some embodiments, the speech-to-text (ASR 208), response-generating AI 214, and text-to-speech 228 are each provided by different models. For example, the speech-to-text (ASR 208) and text-to-speech 228 may be provided by models trained independently from the response-generating AI 214.

In some embodiments, the speech-to-text (ASR 208), response-generating AI 214, and text-to-speech 228 may each be provided by the same model. In such embodiments, one model trained for automatic speech recognition, reply generation, and speech generation may be used.

In some embodiments, the systems described herein may receive conversational data in one or more modalities (e.g., speech, text, video) and convert those modalities into a modality or modalities used by the response generation AI 214. In some embodiments, the systems described herein may be able to convert the modality or modalities of the reply generated by the response generation AI 214 into a delivery modality. In some embodiments, the system converts speech to text for the response generation AI 214 and the textual reply back into speech for the user. In some embodiments, the system may convert speech and/or video into, for example text for the response generation AI 214. In some embodiments, the generated reply may be converted from text into speech and/or video (e.g., an accompanying avatar animation, graphs, etc.). In some embodiments, the response generation AI 214 is configured to process, for example, video, speech, or other data modalities directly. In some embodiments, the system is configured to deliver output in a multi-modal fashion. For example, the system may deliver video or closed captions for the patient. The response generation AI 214 may be multi-modal wherein it is configured to receive information in different modes (e.g., text, speech, video, etc.) and to deliver information in different modes (e.g., text, speech, video, etc.). The system may be configured to use patient information to determine which modes to use (e.g., the system may provide replies in visual or textual format for a patient that is deaf, i.e., not by speech).

In some embodiments, the system may be configured to use multiple modalities for the same or different ends. For example, the system may use both audio and visual data to output responses to a user as part of the conversation. As another example, the system may make use of, for example, conversational data to receive information from the patient, but also use, for example, video data to assess and sense the patient's state.

In some embodiments, the system can be configured to change modalities in real-time. For example, the user may start with a voice conversation, but may elect to switch to a text-based conversation (e.g., if they are headed somewhere that they cannot talk). This may be beneficial as it can continue the conversation (and accordingly keep all cached 225 or contextual information from previous responses) without initiating a new call. This may be more computationally efficient for the system as it does not require an additional initiation of a conversation with the AI Care Manager engine 200 (which may include terminating and summarizing a current session and subsequently using that summary (which may lose some context) to initial a subsequent conversation in a different modality).

In some embodiments, the system may be configured to use different modalities for specific tasks. For example, if the conversation is being orchestrated with audio and video, the conversation itself may be generated based primarily with audio, there may still be specific uses for the video content. This may include, for example determining the user's state. In some embodiments, this may enable the user to 'show' the system things (e.g., body parts for condition assessment or broken pieces of equipment for technical troubleshooting). In the medical context, the system may include an image processing module that may be configured to assess images or streams of images to assess the medical state of a particular condition of the user. This may be orchestrated though the Sensing Engine 117. This may be useful to more efficiently direct the user for appropriate care. This may be useful to assess ongoing treatment efficacy or recovery progress. In such embodiments, computer vision models may extract features from the captured image of the condition location and output features into a specific condition assessment model. There may be multiple condition assessment models trained for different conditions (e.g., the model used to detect the presence of an infection around a cut may differ from the model used to assess the presence of a condition related to the eye). In some embodiments, the model may be trained in an end-to-end fashion (e.g., the model uses image processing to process the image and generate an output regarding the condition). The output of such specific models may be delivered to the AI Care Manager engine 200 as context to guide the conversation (e.g., the AI Care Manager engine 200 may generate a response related to the assessment of the condition).

Having a particular image processing protocol for assessing conditions may also be technically advantageous not only to assess such conditions, but because the system may be configured to selectively activate the protocol. Assessments of a condition in visual information (e.g., by image processing) may be computationally intense. Accordingly, it may not be efficient to leave such a protocol running during the entire duration of the conversation. Instead, the AI Care Manager engine 200 may be configured to activate it if, for example, the user asks to show the AI Care Manager engine 200 something or if the AI Care Manager engine 200 wants to assess something (which may be relevant in a post-treatment follow up session about a particular condition). Accordingly, the AI Care Manager engine 200 may be configured to access such functionality depending on the modality of the conversation and the needs of the conversation.

In some embodiments, the system may be equipped with, for example, image processing models that may be configured to extract features from the images. These extracted features may be used in multiple subsequent models (e.g., an ongoing assessment of the user's state for, for example, conversational engagement and for a condition assessment). Splitting the model up in this manner may make it easier to update various components of the model without necessitating full model training (e.g., end-to-end training). In some embodiments, the computer vision model may be configured in an end-to-end fashion for each function.

In some embodiments, the model may not explicitly convert speech to text for analysis of by the response generation AI 214. In some embodiments, the model may not convert speech to text at all (and not convert text of the generated reply back to speech). For example, the response-generating AI 214 is configured to recognize speech and deliver speech as an output.

In some embodiments, the system may be configured to manage Interactive Voice Response (IVR) systems.

IVR technology can allow users to interact with computer-operated telephone systems through voice or dual-tone multi-frequency inputs. IVR systems often make use of pre-recorded or dynamically generated audio to communicate with a user. The system described herein may encounter such IVR systems, for example, for a voice mail service, to navigate a call routing system, or if a wrong number is dialed. IVR systems may impact the output. For example, the system may attempt to communicate with an IVR system. For example, if the IVR system provides the option of leaving a message, then the AI Care Manager engine 200 may be configured to leave a message with the user. The AI Care Manager engine 200 may select its response based on user preferences (e.g., has the user indicated they want the AI Care Manager engine 200 to leave a message).

In some embodiments, the system 100 or 101 is configured to recognize audio arising from an IVR system and reject the call or navigate through the IVR system to reach the patient. This may be handled as part of the input guardrail 210 or as part of another component of the system 100 or 101.

In some embodiments, IVR systems may be recognized based on the words and phrases used common to IVR systems (e.g., "press 1 for . . . ", "please hang up and try your call again", etc.). In some embodiments, IVR systems may be recognized by the particular audio patterns that they exhibit (e.g., where there is a patient speaker and an IVR speaker, the system 100 or 101 may identify the monotonic, professional, and vaguely cheery speaker as the IVR speaker). In some embodiments, the system may be trained on sample IVR systems to quickly identify the IVR systems and manage that data accordingly.

In some embodiments, the system may generate updates and alerts throughout the system. For example, should a red flag present during a conversation (e.g., sound of a fall) then the system may be configured to ask the patient if they are alright and, absent a response, alert other members of the care team (or call 911 or other emergency service). The alerts may also provide the care team with updates about the patient's state (the care team may be able to personalize these updates). The system may be able to alert the patient to updates provided to the care team based on their conversation outcomes.

The alerts may be events or event-driven architectures. For example, the system may enable different participants to subscribe to updates about the patient. When an event happens, the system can publish the event and that is sent to those who are subscribed to receive it (subject to data access restrictions). The subscriber can then elect to take further actions based thereon.

In some embodiments, the system may be configured to help the patient fill out information of a form or other 3rd party software with the assistance of a bot. For example, the bot may be able to provide the patient with assistance to fill out a form even when the bot had not previously been trained using the form. For example, the system may exhibit behavior that resembles creative collaboration and problem solving. The system may ask a series of questions to reveal the potential for a better (desired outcome producing) conversation (e.g. switch modality, add modality, remove modality, etc.).

In such embodiments, the system described herein may be capable of presenting a form to the user (as part of its reply delivery) and guiding the user through the completion of the form. For example, the system may present the form to the user and prompt the user to give the system the information which the system then inputs on the user's behalf. The user can review the information as it is entered. The output may be a completed form. Such an implementation may be useful when, for example, completing a survey with a user or enrolling a user in a program.

In some embodiments, the user may be able to redirect the call to a human agent 240 themselves. This option may be delivered to the user when the call starts (e.g., the system may start with a message informing the patient with as much). For example, the user may not wish to engage with the AI Care Manager engine 200 and may immediately request to speak with a human agent 240. The AI Care Manager engine 200 may be configured to detect such a request and immediately defer the call to a human agent 240. For example, the input guardrail 210 may be configured to detect a statement that makes such a request and immediately refers the call to a human agent 240. Handling the call in this way can prevent the response-generating AI 214 from using any processing power which may relieve some strain on any computing resources used to orchestrate this system 100/101 at scale.

In some embodiments, the AI Care Manager engine 200 may be configured to access standard rules, practices, and/or databases to assess the safety in a medical application case. For example, the AI Care Manager engine 200 can be configured to query the standard rules, practices, and/or databases for the latest practices, medical guidelines, etc. The technical advantage of such a configuration may allow the AI Care Manager engine 200 to be updated just by updating the resources available within the standard rules, practices, and/or databases. These queries may be conducted in real-time during the conversational session. For example, the response-generating AI 214 may query the standard rules, practices, and/or databases to formulate a response to a user input. As another example, the output guardrail 226 may query the standard rules, practices, and/or databases to determine whether the output is going to be safe (e.g., medically accurate and, optionally, not inclusive of medical advice).

Model Context Protocol (MCP) & External Tool Integration

In some embodiments, the systems described herein can execute a method of dynamic tool selection and the security "handshake" required for handling Protected Health Information (PHI). The system can use a standardized interface layer or API schema (e.g. model context protocol (MCP)) configured to facilitate secure, bi-directional data exchange between the core foundational model (e.g., LLM, multimodal, world model) and a plurality of external, domain-specific utilities. This protocol can act as a translation layer, converting natural language intent from the agent into executable syntax for external software, and formatting the outputs back into context for the agent.

List of Possible Connected Tools

In some embodiments, the systems described herein may make use of external information sources. Such sources may include, for example, Electronic Health Record (EHR) Systems (e.g., Epic) to, for example, read/write patient history and vitals; Pharmacological Databases (e.g., RxNorm, First Databank) for, for example, checking drug-drug interactions and dosage guidelines; Medical Literature Repositories (e.g., PubMed, UpToDate) for, for example, retrieving evidence-based clinical guidelines; Diagnostic Imaging Servers (e.g., PACS/DICOM viewers) to, for example, access X-rays or MRI metadata; Appointment Scheduling APIs for, for example, checking provider availability and booking slots; or Wearable IoT Data Streams: (e.g., Apple HealthKit, Glucometers) for, for example, real-time remote patient monitoring.

Agent-to-Agent (A2A) Communication Protocol

In some embodiments, the systems described herein can provide methods of conflict resolution between agents (e.g., if the Billing Agent contradicts the Clinical Agent) and preservation of context during a "hand-off." The system can use a structured communication framework (e.g. agent-to-agent A2A) allowing distinct autonomous agents to collaborate, negotiate, and hand off tasks. This protocol defines a standard message format (headers for intent, payload for medical data, and security tokens) that enables a "swarm" architecture. For example, a "Triage Agent" utilizes this protocol to securely transmit patient state and preliminary analysis to a specialized "Cardiology Agent" or "Billing Agent" without human intervention. This allows the proposed system to connect to other agents the client is using.

Orchestration Architectures

In some embodiments, the systems described herein can generate an optimum response to satisfy customers. The system can access internal and external tools, other AI agents, RAG, human agents, and memory. The system can be implemented via two distinct embodiments regarding how tasks are managed and routed.

The first embodiment (Deterministic Pipeline Architecture) may be a state-based control system where conversation flow is managed by a pre-defined logic graph or static routing table. Incoming audio/text data streams can be processed through a fixed sequence of functional nodes in order to produce response. This method relies on hard-coded decision trees to ensure strict adherence to clinical protocols, minimizing hallucination risks by restricting the agent to approved pathways.

The second embodiment (Hierarchical "Cognitive Controller" Architecture) may be a dynamic system utilizing a central "Thinking LLM" (Reasoning Engine) that acts as an orchestrator for a sub-layer of "Non-Thinking" (specialized/task-specific) LLMs. The Thinking LLM can maintain the global state of the interaction, evaluate the patient's complex needs in real-time, and dynamically delegate sub-tasks to smaller, faster models (e.g., a summarization model or a coding model). This architecture can self-correct and alter its own workflow based on the conversation's emotional or clinical nuance.

Infinite Context Windows

In some embodiments, the systems described herein can cross-reference a symptom from, for example, 20 years ago with a current complaint (a correlation impossible for standard context windows or human recall) to identify rare patterns or misdiagnoses. The system can be built so it can be easy to extend a case in which technology is able to process almost infinite size of information without hallucination and misinformation. Given data ingestion and processing methods that enable the medical agent to simultaneously analyze massive datasets without information loss or "sliding window" truncation, the system can support additional use cases to better support a medical journey of patients. In a medical context, this can allow the system to ingest a patient's entire lifelong medical history (every lab result, clinical note, and genetic marker from birth to present) along with vast libraries of medical textbooks. The system can allows for easy addition of tools, processes, and external AI agents to allow for this.

Long-Term Memory and Fact Retrieval

In some embodiments, the systems described herein can provide a mechanism for "memory consolidation" which may automatically extract clinically significant entities from a conversation after it closes, validate the clinically significant entities, and update the patient's longitudinal profile. This can prevent the agent from asking the same questions in subsequent visits. The system can implement a dual-store memory architecture comprising a "Session Buffer" (working memory for the current interaction) and a "Semantic Knowledge Store" (long-term database). This system can use vector embeddings to index and persist key facts (e.g., "Patient is allergic to penicillin" or "Patient prefers evening appointments") and/or summaries of previous conversations across disparate sessions. The facts can be persisted within graph-based and/or vector-based storage depending on use case and customer.

Figure 3:
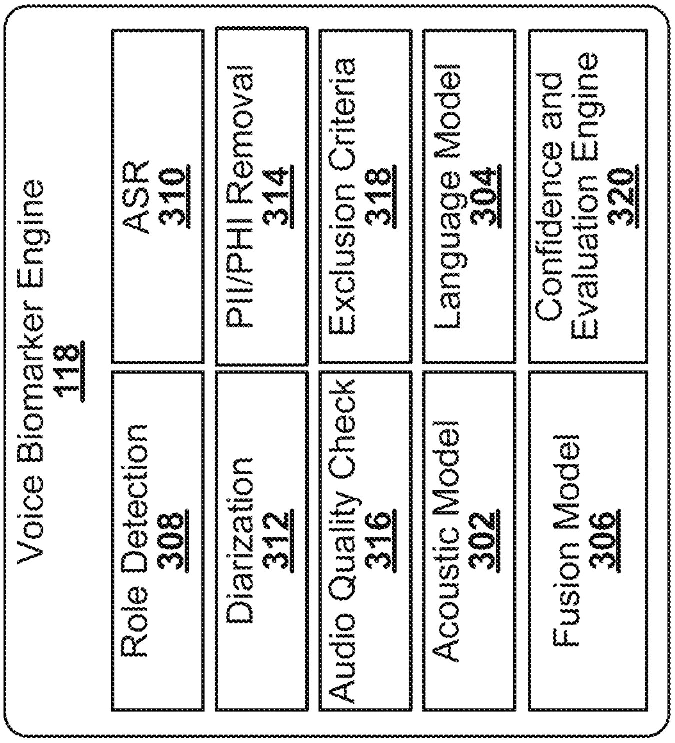
FIG. 3 shows a process diagram for an example method of processing and generating a conversation, according to some embodiments.

FIG. 3 shows an example architecture for the vocal biomarker engine 118, according to some embodiments.

In some embodiments, the system 100 or 101 may be configured to assess the patient for any conditions (e.g., physical or mental or behavioural health conditions) during the assessment. This may be done in a passive manner, for example, the vocal biomarker engine 118 may passively listen to the conversation the patient has with the AI Care Manager engine 200 (or a human agent 240) to assess the patient (e.g., determine the presence, absence, and/or severity of a condition).

In some embodiments, the vocal biomarker engine 118 may be configured to provide feedback to the AI Care Manager engine 200 during the conversation which may prompt the AI Care Manager engine 200 to inquire about certain topics with the patient to generate a better assessment. For example, the AI Care Manager engine 200 may be configured to ask about known conditions, but during the conversation with the patient, the vocal biomarker engine 118 may identify that the patient is suffering from an additional condition. In such a circumstance, the vocal biomarker engine 118 may be configured to prompt the AI Care Manager engine 200 to follow up with questions about that condition to help determine whether the patient does have the condition and/or the severity of the condition or symptomatology thereof (e.g., it may dynamically update the conversational objectives of the AI Care Manager engine 200). In some embodiments, the AI Care Manager engine 200 may be configured to turn the vocal biomarker engine 118 on or off in real-time based on conversational objectives (e.g., the conversation may start with the vocal biomarker engine 118 activated, but may terminate its function once a degree of confidence that the patient is not exhibiting new conditions). This may save computer processing power.

In some embodiments, the vocal biomarker engine 118 may be made up of one or more acoustic models 302 and language models 304. The acoustic model 302 may be configured to assess the patient's acoustic data (e.g., speech cadence, pauses, filler words, sighs, etc.) from the conversational data. The language model 304 may be configured to assess the patient's semantic data (e.g., topics of conversation, word choice, etc.). These models 302 and 304 may be configured to generate an output predicting whether the patient has a condition (e.g., a mental or behavioural condition) and/or the severity of the same. In some embodiments, where both models 302 and 304 are present, there may additionally be a fusion model 306 configured to fuse the outputs from the acoustic model 302 and the language model 304 to generate a composite output. The outputs from the acoustic model 302 and the language model 304 may be dynamically weighted in temporal segments based on, for example, topic of conversation, role of current speaker, quality of audio data, etc.

In some embodiments, one or more of the acoustic models 302, the language models 304, and/or the fusion models 306 can comprise one or more machine learning models. In some embodiments, additional models may be present. For example, should visual data of the patient be available (e.g., a video call), then the visual data may also be processed using, for example, a visual model comprising a machine learning model to generate a visual output. This output may be fused with the other model outputs by the fusion model 306.

In some embodiments, the vocal biomarker engine 118 may further be equipped with role detection 308. The role detection 308 may be configured to detect the roles of the speakers in the conversation. This may be useful in circumstances where the system is passively listening to a conversation and the patient and agent or other healthcare professional are coming through on the same channel. This may also be useful where the patient is accompanied on the call by another caregiver (e.g., a family member). The role detection 308 can be used to attribute portions of the conversation to the patient as opposed to those of the agent or another caregiver. This can ensure that, for example, the acoustic data from the caregiver is not weighted highly to diagnose the patient. The role detection can also inform vocal biomarker engine 118 if the conversation contains only agents in the call or if it contains some patients/caregivers.

In some embodiments, the vocal biomarker engine 118 may further be equipped with automatic speech recognition 310. In some embodiments, the automatic speech recognition may be the same or different as that carried out in the AI Care Manager engine 200 (e.g., by automatic speech recognition 208). In some embodiments these may be carried out by different automatic speech recognition engines (e.g., where the vocal biomarker engine 118 has been trained with a specific automatic speech recognition engine 310 or where this processing is being carried out by different processors).

In some embodiments, the vocal biomarker engine 118 may be configured to translate conversational data. For example, the vocal biomarker engine 118 may translate the conversational data before putting the conversational data through an automatic speech recognition engine 310. In some embodiments, the automatic speech recognition engine 310 may be configured to translate the speech data while converting it to text. In some embodiments, the text produced by the automatic speech recognition engine 310 may be subsequently translated.

In some embodiments, the vocal biomarker engine 118 may further be equipped with diarization 312. Diarization 312 may diarize the conversations between the AI Care Manager engine 200 and the patient. This may be useful to generate subsequent summaries of the conversations with the patient. These summaries may be used to later brief a human agent 240 or it may be used subsequently by the AI Care Manager engine 200 for context in future conversations with the patient.

In some embodiments, the vocal biomarker engine 118 may further be equipped with PII/PHI removal 314. The PII/PHI removal 314 may remove personally identifiable information (PII) and personal health information (PHI). This may be useful to ensure that sensitive information is not used or saved within the vocal biomarker engine 118 in a manner that breaches local regulations.

In some embodiments, the vocal biomarker engine 118 may further be equipped with audio quality check 316. The audio quality check 316 may check that the input data is of sufficient quality to be used by the system for prediction. It may be configured to reject audio that is of insufficient quality. This may protect the predictions made by the vocal biomarker engine 118 from being damaged by poor audio quality.

In some embodiments, the vocal biomarker engine 118 may further be equipped with exclusion criteria 318. The exclusion criteria can remove calls when it meets certain criteria. These criteria may include the identification of an IVR, detection of only the agent on the call (i.e., patient did not speak), the patient was too far from the device, the patient hasn't spoken enough, the patient hasn't provided enough cues for assessment, etc.

In some embodiments, the vocal biomarker engine 118 may further be equipped with confidence and evaluation engine 320. The confidence and evaluation engine 320 may evaluate the outputs generated by the vocal biomarker engine 118. It may provide such evaluations with the output. The confidence and evaluation engine 320 may use the confidence to determine when to intervene in the AI Care Manager 200 conversation (e.g., it may wait until a particular state is detected and a threshold confidence that that state is accurate is achieved before intervening in the conversation). In some embodiments, the confidence and evaluation engine 320 may provide confidences for time-segments of the conversation and weight those segments accordingly (e.g., it may determine that a specific segment in the conversation had poor audio quality and weight that segment lower).

In some embodiments, the AI Care Manager engine 200 can be configured to direct which vocal biomarker engine 118 is to be used. For example, the AI Care Manager engine 200 may select between vocal biomarker engines 118 that are configured to predict different conditions, to receive conversational data in different modalities (e.g., text, voice, video, etc.), or to receive information in different languages. This may change the vocal biomarker engine 118 or parts thereof (e.g., it may change the language model 304 in a case where it is receiving information in a different language).

Other sensing engines than the vocal biomarker engine 118 may be used for one or more other modalities of user sensing. These different engines may be implemented individually or collectively (e.g., using a fusion engine). The system may be configured to assess the patient's voice to sense the patient's state. In some embodiments, the system may make use of video (e.g., to determine patient gaze). In some embodiments, the system may take into account metadata about the patient (e.g., time of day, medications being taking, etc.) to help assess the patient's state.

In some embodiments, the patient state can relate to one or more of emotional state, health state (e.g., including fatigue, being hungry, etc.), mental health state, stress, rush, confusion (e.g., general confusion or confusion about the conversation itself), engagement state (e.g., is the patient engaged or bored and disengaged), distraction state (e.g., from interruptions), fluency state (in the language used), etc.

The user state may also be provided to the AI Care Manager engine 200 to further assist the conversation (e.g., it may identify that the user is confused to suggest the AI Care Manager engine 200 explain the previous concept more simply).

Optionally, the devices, systems, and methods described herein may be used to implement aspects of the devices, systems, and methods in U.S. Pat. No. 10,748,644, titled "Systems and methods for mental health assessment", filed Sep. 4, 2019, the entirety of which is incorporated by reference herein. Accordingly, the devices, systems, or methods described herein may be interoperable with a method for identifying whether a subject is at risk of having a mental or physiological condition, comprising obtaining data from said subject, said data comprising conversation data and optionally associated visual data, processing said data using a plurality of machine learning models comprising a natural language processing (NLP) model and an acoustic model to generate an NLP output and an acoustic output, wherein said plurality of machine learning models comprises a neural network trained on labeled conversation data collected from one or more other subjects, wherein said labeled conversation data for each of said one or more other subjects is labeled as (i) having, to some level, said mental or physiological condition or (ii) not having said mental or physiological condition, fusing said NLP output and said acoustic output by (1) applying weights to said NLP output and said acoustic output to generate weighted outputs and (2) generating a composite output from said weighted outputs, wherein said NLP output and said acoustic output each comprise a plurality of outputs corresponding to a plurality of time segments of said conversation data, and wherein said weights in (1) are temporally-based, and outputting an electronic report identifying whether said subject is at risk of having said mental or physiological condition, based at least on said composite output, which risk is quantified in a form of a score having a confidence level provided in said report.

Optionally, the devices, systems, and methods described herein may be used to implement aspects of the devices, systems, and methods in U.S. patent application Ser. No. 17/493,687, titled "Confidence evaluation to measure, trust in behavioral health survey results", published as US Patent Application Publication No 20220270716 A1, filed Oct. 4, 2021, the entirety of which is incorporated by reference herein. Accordingly, the devices, systems, or methods described herein may be interoperable with a method for measuring a degree of confidence in a reliability of responses received from a human subject in a health survey for evaluating a health state of the subject, the method comprising obtaining response data that is generated by the subject in response to prompts presented to the subject during administration of the health survey to the subject, wherein the response data comprises a plurality of conditioning events and a plurality of conditioned events, determining a first probability that a first conditioned event is present in the response data based in part on a presence of a first conditioning event in the response data, wherein the plurality of conditioning events comprises the first conditioning event and the plurality of conditioned events comprises the first conditioned event, and wherein the first probability is used to determine a first event pair comprising the first conditioned event and the first conditioning event, repeating steps the first two steps for two or more other conditioned events and other conditioning events to generate a plurality of additional probabilities for a plurality of additional event pairs, and combining two or more probabilities selected from (i) the first probability and the plurality of additional probabilities or (ii) the plurality of additional probabilities to generate a confidence vector data, wherein the confidence vector data represents a measure of confidence in the reliability of the subject that generated the response data in response to the health survey.

Optionally, the devices, systems, and methods described herein may be used to implement aspects of the devices, systems, and methods in U.S. Patent Application Ser. No. 17/726,999, titled "Acoustic and natural language processing models for speech-based screening and monitoring of behavioral health conditions", published as US Patent Application Publication No 20220328064 A1, filed Apr. 22, 2022, the entirety of which is incorporated by reference herein. Accordingly, the devices, systems, or methods described herein may be interoperable with a method for detecting a behavioral or mental health condition in a subject, said method comprising obtaining a speech sample comprising one or more speech segments from said subject, performing at least one of (i) or (ii), wherein (i) comprises processing said speech sample with at least one acoustic model comprising an encoder to generate an acoustic model output comprising an abstract feature representation of said speech sample, wherein said encoder is pretrained to perform a first task other than detecting said behavioral or mental health condition in said subject, and (ii) comprises processing said speech sample, a derivative thereof, and/or said speech sample as transcribed to a text sequence, with at least one natural language processing (NLP) model to generate a language model output, and using at least one of said acoustic model output or said language model output, to individually or jointly generate an output indicative of whether said subject has said behavioral or mental health condition.

Optionally, the devices, systems, and methods described herein may be used to implement aspects of the devices, systems, and methods in U.S. patent application Ser. No. 18/263,650, titled "Systems and methods for multi-language adaptive mental health risk assessment from spoken and written language", published as US Patent Application Publication No 20240087752 A1, filed Feb. 3, 2022, the entirety of which is incorporated by reference herein. Accordingly, the devices, systems, or methods described herein may be interoperable with a method for detecting a behavioral or mental health condition, the method comprising receiving an input signal comprising a plurality of audio or lexical characteristics of speech of a subject, wherein at least one of the plurality of audio or lexical characteristics of the speech relates to at least one language, based at least in part on the plurality of audio or lexical characteristics of the input signal, selecting one or more acoustic or natural language processing (NLP) models, wherein at least one of the acoustic or NLP models is a multi-lingual, a model with a model language that includes the at least one language, a model with a model language and translating the input signal from the at least one language to the model language, or a model with a model language and translating the model from the model language to the at least one language, and detecting a result estimating a severity of risk of having the behavioral or mental health condition by processing the input signal with a fused model or joint model derived from the one or more acoustic or NLP models.

Optionally, the devices, systems, and methods described herein may be used to implement aspects of the devices, systems, and methods in PCT Patent Application No. PCT/US2024/033710, titled "Systems and Methods for predicting Mental Health Conditions based on Passive Processing of Conversational Speech and Language", filed Jun. 13, 2024, the entirety of which is incorporated by reference herein. Accordingly, the devices, systems, or methods described herein may be interoperable with a system for identifying roles of speakers in a conversation. The system including at least one input device for receiving conversation data from at least one user, at least one output device for outputting an electronic report, and at least one computing device in communication with the at least one input device and the at least one output device. The at least one computing device configured to receive the conversation data from the at least one input device, determine at least one role of at least one speaker, process the conversation data to generate a language model output and/or an acoustic model output, apply weights to the language model output and/or the acoustic model output, generate an electronic report, and transmit the electronic report to the output device. The language model output and the acoustic model output each including a plurality of outputs corresponding to a plurality of time segments of the conversation data. The weights are optionally temporally-based, and wherein the weights are based in part on the at least one role of the at least one speaker during each time segment. Accordingly, the devices, systems, or methods described herein may be interoperable with a system for identifying topics in a conversation. The system includes at least one input device for receiving conversation data from at least one user, at least one output device for outputting an electronic report, and at least one computing device in communication with the at least one input device and the at least one output device. The at least one computing device configured to receive the conversation data from the at least one input device, process the conversation data to generate a language model output, apply weights to an output to generate a weighted output, generate an electronic report, and transmit the electronic report to the output device. The language model output includes one or more topics corresponding to one or more time ranges. The output includes a plurality of outputs corresponding to a plurality of time segments of the conversation data. The weights are optionally temporally-based. The weights are based in part on the one or more topics during each time segment. Accordingly, the devices, systems, or methods described herein may be interoperable with a system for scoring surveys based on a conversation. The system includes at least one input device for receiving conversation data from at least one user, at least one output device for outputting an electronic report, at least one computing device in communication with the at least one input device and the at least one output device. The at least one computing device configured to receive the conversation data from the at least one input device, process the conversation data to generate a language model output, generate an electronic report, and transmit the electronic report to the output device. The language model output includes an identification of at least one query based on conversation data from an agent and at least one response to the at least one query based on the conversation data from a patient. The at least one query is mapped onto a predefined query and the at least one response to the at least one query is mapped onto a predefined response to the predefined query.

According to an aspect, there is provided a system 100, 101 to drive a conversation with a user. The system 100, 101 including a hardware processor 152 including a response-generating AI 214 may include a knowledge base 216 and/or an LLM 222, a multimodal, and/or a world model (e.g., ones that can work with, for example, video, text, and audio together), and memory 154 for storing instructions executable by the hardware processor 152. When executed by the hardware processor, the instructions cause the system 100, 101 to receive conversational data from a user, embed the conversational data using embedding model 212, generate a reply using a response-generating AI 214 to process the embedded conversational data and context from the knowledge base 216, transmit the generated reply.

In some embodiments, the system may further include tools and other agents.

In some embodiments, the system 100, 101 further includes a vocal biomarker engine 118 configured to predict and/or assess whether the user has a physical, mental, or behavioural health condition or the severity of same.

In some embodiments, the system 100, 101 is further configured to predict one or more of global states of the user, moment-to-moment states of the user, context of a user environment. The global states of the user refer to states like conditions which are no likely to change during the course of the conversation (e.g., that the user has depression). Moment-to-moment states refer to less long lasting states that may be influenced by the course of the conversation (e.g., confusion, boredom, etc.). Context of the user environment may refer to ambient noise in the user's environment. These features may be used to further drive system behaviours.

In some embodiments, the instructions further cause the system 100, 101 to determine utility of the generated reply based on subsequent conversational data and to update the response-generating AI 214 based on the utility of the generated reply.

In some embodiments, the system 100, 101 further includes a process engine 119 configured to generate and act on tasks based on the conversation.

In some embodiments, the process engine 119 is configured to generate and act on the tasks based on patient information. In some embodiments, tools and AI agents 221 can be used to act of the tasks. For example, the AI care manager engine 200 may be configured to interface with AI agents of other systems to act on tasks.

In some embodiments, the process engine is configured to interface with external systems to retrieve the patient information or to act on the tasks.

In some embodiments, the response-generating AI 214 processes the embedded conversational data using cached conversational data, wherein the cached conversational data comprises prior embedded conversational data provided by the user.

In some embodiments, the context includes a conversational objective and a conversational task, the conversational task is used to generate the reply and the conversational objective is a goal of the conversation, and the instructions cause the system 100, 101 to determine utility of the generated reply in achieving the conversational objective based on subsequent conversational data, and update the conversational tasks based on the utility of the generated reply.

In some embodiments, transmitting the generated reply comprises providing the generated reply to a human agent 240, wherein the generated reply is a suggested next response or action or direction.

In some embodiments, transmitting the generated reply comprises delivering the generated reply to the user.

In some embodiments, the response-generating AI 214 is configured to access electronic medical records.

In some embodiments, the response-generating AI 214 is configured to use patient healthcare metadata.

In some embodiments, the conversational data is processed by an input guardrail 210 to classify the conversational data as bad or good.

In some embodiments, the input guardrail 210 processes the conversational data by determining that the conversational data exhibits one or more of unintelligibility, inappropriate behaviour, and inappropriate topic.

In some embodiments, the conversational data is embedded when the conversational data is classified as good or the input guardrail 210 carries out remediation when the conversational data is classified as bad. In some embodiments, the input guardrail 210 redirects the conversation to a human agent 240 upon classifying the conversation data as bad. In some embodiments, the conversation data is classified as bad after remediation fails. In some embodiments, the human agent 240 is provided with a summary of the conversation and/or a summary of a reason for the bad classification.

In some embodiments, the generated reply is processed by an output guardrail 226 to classify the generated reply as good or bad In some embodiments, the output guardrail 226 processes the generated reply by determining that the generated reply exhibits one or more of unresponsiveness, inaccuracy, harmful information, and inappropriate topic.

In some embodiments, the generated reply is transmitted to the user when the generated reply is classified as good or the output guardrail 226 carries out remediation when the generated reply is classified as bad. In some embodiments, the output guardrail 226 redirects the conversation to a human agent 240 upon classifying the conversation data as bad. In some embodiments, the conversation data is classified as bad after remediation fails. In some embodiments, the human agent 240 is provided with a summary of the conversation and/or a summary of a reason for the bad classification.

In some embodiments, the response-generating AI 214 is pre-loaded with context and/or memory 223 from one or more of prior conversations with the user, health records about the user, conversational objectives prior medical knowledge, user preferences, healthcare provider preferences. In some embodiments, the response-generating AI 214 is pre-loaded with context and/or memory 223 from one or more of patient and healthcare providers using tools and A2A (agent-to-agent) or similar communications with external systems.

In some embodiments, the conversational data is converted to text using an automatic speech recognition engine 208.

In some embodiments, the generated reply is converted to speech using a text-to-speech engine 228 that can provide the generated speech as one of a plurality of custom voices 230.

In some embodiments, the system 100, 101 is configured to elicit information for or provide information on one or more of medication reconciliation, diet, exercise, social determinants of health, living situation, assessment of severity of depression and anxiety symptomatology, substance use, assessment of cognitive availability, assessment of ability to perform activities of daily living, care pathways, clinical protocols, claims eligibility, claims adjustment, claims dispute, claims issues, pharmaceutical benefits, prior authorizations, and pre-admission, post-discharge, and ongoing care management factors, or the like.

In some embodiments, the system 100, 101 is used for one or more of a medical follow up conversation, a patient intake conversation, an insurance intake conversation, or a troubleshooting technology conversation.

In some embodiments, the response-generating AI 214 accesses a user profile comprising user preferences or personalizations to tailor the generated reply or the conversation. In some embodiments, the user profile may impact how the response-generating AI 214 approaches the conversation as a whole (e.g., overall settings). In some embodiments, the user profile may impact how the response-generating AI 214 formulates a particular reply.

In some embodiments, these preferences or personalizations may be provided by the user upon enrollment. In some embodiments, these preferences or personalizations may developed automatically as the system 100, 101 identifies what the user responds to (e.g., by assessing conversations and determining what types of replies elicited good input from the user on the next conversational turn). In some embodiments, the personalizations in the user profile are set by a healthcare professional in the clinical workflow. The health care professional may want the system 100, 101 to behave a certain way for their own use, and/or for that particular patient.

In some embodiments, the conversational data includes spoken language, text, or video.

In some embodiments, the system 100, 101 is configured to be multilingual. In some embodiments, the system 100, 101 detects a language of the conversational data prior to embedding the conversational data and uses the detected language to embed the conversational data, select an embedding model, response-generating AI 214, input guardrail 210, or output guardrail 226, or translate the conversational data.

Some embodiments further include a sensing engine 117 configured to assess the user. In some embodiments, the sensing engine may be or may communicate with a vocal biomarker engine 118.

In some embodiments, the sensing engine 117 receives a captured image of the user, processes the captured image with an image processing model to extract features from the captured image, processes the extracted features to generate a user assessment; and transmits the user assessment to the response-generating AI.

General System Operation

Figure 4:
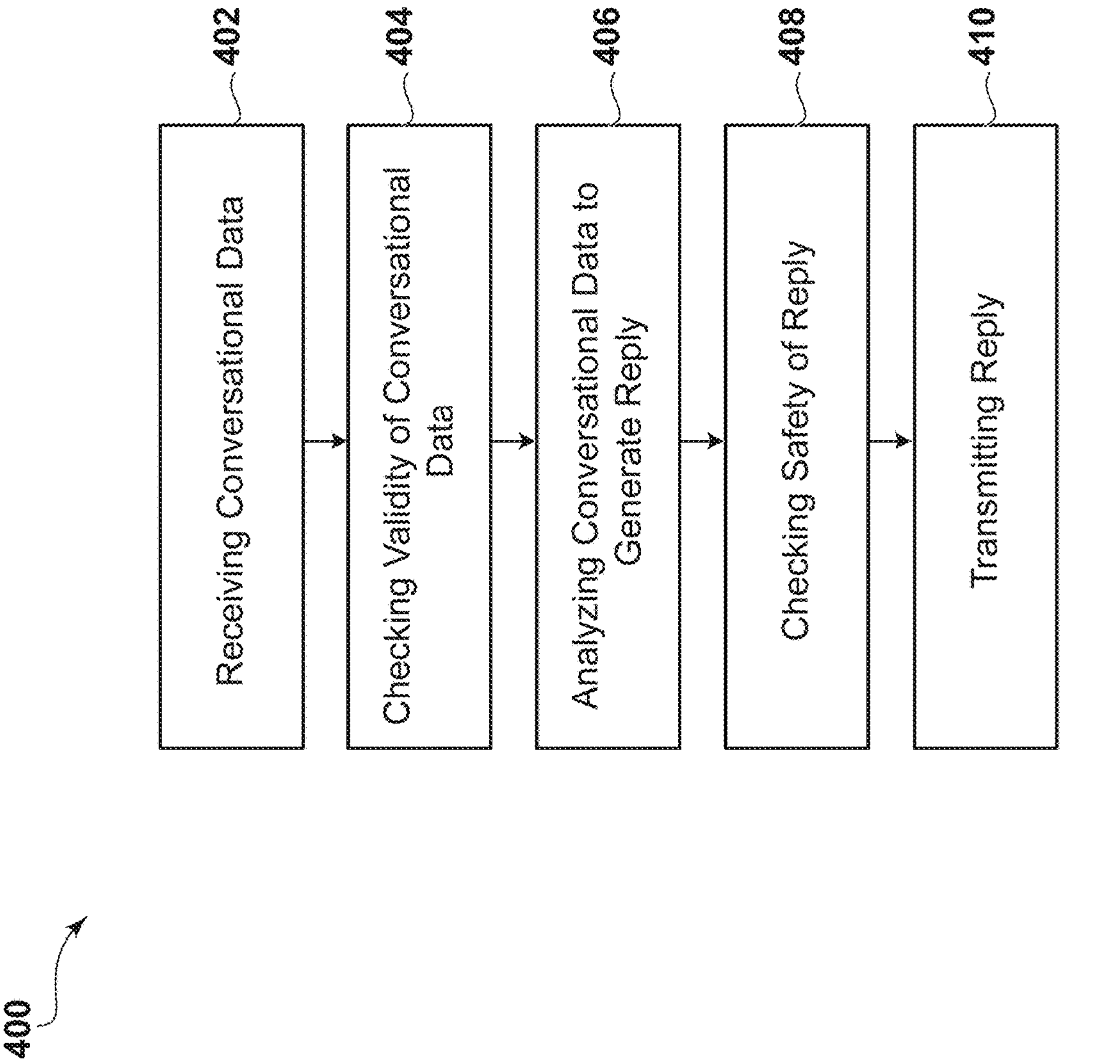
FIG. 4 shows a process diagram for an example method of processing and generating a conversation, according to some embodiments.

FIG. 4 shows a process diagram for an example method 400 of processing and generating a conversation, according to some embodiments.

The method 400 includes receiving input conversational data (block 402), checking the validity of the input conversational data (block 404), analyzing the conversational data to generate a reply (block 406), checking the safety of the generated reply (block 408), and transmitting the generated reply (block 410).

Referring to receiving the input conversational data (block 402), the input conversational data may be received from the user in any manner of ways. For example, the user may provide input conversational data via a telephone 160 which may be facilitated with a SIP/VoIP engine 104. As another example, the user may provide input conversational data via an app 174 running on a user device 170. In some embodiments, the input conversational data may be converted to text using an automatic speech recognition engine 208. In some embodiments, the input conversational data may be translated into a model language. While the foregoing has generally described input conversational data received in an audio format, embodiments described herein may also receive input conversational data in, for example, text format (e.g., the AI Care Manager engine 200 may be configured to receive text messages) and/or video format.

In some embodiments, the method may also include transforming the conversational data into a format acceptable by the system. In some embodiments, this may include transcribing the conversational data into transcribed input conversational data.

Referring to checking the validity of the input conversational data (e.g., in the form of transcribed conversational data) (block 404), an input guardrail 210 may identify whether the textual conversation is intelligible (e.g., transcribed properly, generally comprehensible), includes appropriate behaviour (e.g., not behaving in a manner the AI Care Manager engine 200 is not trained to respond to), and includes appropriate topics (e.g., not asking about a topic that the AI Care Manager engine 200 should not respond to). If the input guardrail 210 classifies the conversation as bad, then it may bypass conversational data processing and have the AI Care Manager engine 200 ask the user a clarifying question or make a clarifying statement or it may use the classification of the conversation to generate a reply for the user. The input guardrail 210 may be configured to direct the user to a human agent 240. If the conversational data is classified as good by the input guardrail 210, then the conversational data may proceed to the remaining method steps.

Referring to analyzing the conversational data to generate a generated reply (block 406), the conversational data may be embedded using an embedding model 212. The embedded conversational data along with any context may be fed into the response-generating AI 214 (e.g., to the LLM 222). The response-generating AI 214 may use the context which may include user information that was pre-loaded into the AI Care Manager engine 200 such as information about the patient, conversational objectives (e.g., things the AI Care Manager engine 200 needs to inquire about), or information about prior conversations with the patient. The response-generating AI 214 may also receive cached information (e.g., prior embedded conversational data provided to the AI Care Manager engine 200 or prior responses generated) from cache 225. The information may be provided to the response-generating AI 214 using custom prompts 224. The response-generating AI 214 may then generate a reply for the user. In some embodiments, the AI Care Manager 200 may include a response-generating AI 214 which may comprise an LLM 222 and a knowledge base or vector database 216. In some embodiments the response-generating AI 214 may be a Retrieval-Augmented Generation AI. In some embodiments, the response-generating AI 214 is configured to leverage an intrinsic model with externally accessible data to deliver responses.

Referring to checking the safety of the reply (block 408), an output guardrail 226 may identify whether the generated reply is responsive (e.g., to any patient queries), accurate (e.g., correct information being delivered), not harmful (e.g., not providing instructions to the patient likely to harm them or others, e.g., allergies), and not on an inappropriate topic (e.g., it does not attempt to prescribe a medication). If the output guardrail 226 classifies the reply as bad, then it may attempt to regenerate the reply (e.g., using the reply classification). The output guardrail 226 may be configured to direct the user to a human agent 240. If the conversational data is classified as good by the output guardrail 226, then the reply may proceed to the remaining method steps.

In some embodiments, the reply may be transformed. For example, custom voices may be used to transform a textual reply into a natural language audio reply that can be output by the system. This may make the experience more relatable, enjoyable and easier to access for some patients. In some embodiments, vocal biomarker engine 118 or other engines may inform the AI Care Manager engine 200 on the speed of reply or inform the response-generating AI 214 that the person is, for example, confused (and may prompt the AI Care Manager engine 200 to clarify previously delivered information).

Referring to transmitting the reply (block 410), the generated reply may be converted to speech, for example, using a text-to-speech engine 228 for conversations that include speech. The text-to-speech engine 228 may be configured to use custom voices 230. The custom voices 230 may be selected based on which is predicted to provide the best user outcomes (e.g., which voice is predicted to generate the most engagement from that user). While the foregoing has generally described a generated reply that's to be delivered in an audio format, embodiments described herein may also provide the generated reply to the user in, for example, text format (e.g., the AI Care Manager engine 200 may be configured to deliver text messages to the user) and/or video format (e.g., an avatar or other representation of an agent).

In some embodiments, the method 400 may further include generating and actioning tasks based on the conversation using a process engine 119. The AI Care Manager engine 200 may be configured to identify various tasks that may be actioned based on the conversation. The AI Care Manager engine 200 may be configured to inquire with the user about these topics or it may be configured to react to spontaneous statements from the user (e.g., where the user provides information about a task even where the AI Care Manager engine 200 wasn't asking about it). In some embodiments, the AI Care Manager engine 200 may be configured to ask further questions of the user when the topic emerges from a spontaneous statement. The process engine 119 may be configured to interface with various external systems to action the tasks. For example, the process engine 119 may be configured to order refills for the user or coordinate transportation with a taxi service for the user.

In some embodiments, the method 400 may further include predicting whether the user has a physical or mental or behavioural health condition or the severity of same using a vocal biomarker engine 118. In some embodiments, the vocal biomarker engine 118 may be configured to assess the user using one or more of the acoustic models 302 and language models 304. In some embodiments, the outputs of a plurality of models 302 and 304 may be fused using a fusion model 306. The fusion model 306 may be configured to apply weights to temporal segments output but the plurality of models 302 and 304 to generate a composite model output. In some embodiments, the vocal biomarker engine 118 may passively listen to the conversation conducted by the AI Care Manager engine 200. In some embodiments, the vocal biomarker engine 118 may be configured to provide information to the AI Care Manager engine 200 to direct the conversation in real time. In some embodiments, the AI Care Manager engine 200 may be configured to turn the vocal biomarker engine 118 on or off.

In some embodiments, the method 400 may further include evaluating the performance of the method 400. For example, the outputs of the method 400 may be provided to an expert (e.g., a physician) to check. The method 400 may be further improved based on a comparison of the method 400 output and of the expert's decisions. This may include bringing up or not bringing up certain topics at certain times. It may also include any assessments rendered by the system about the patient. The method 400 may further be improved using machine learning methods.

The method 400 may be configured to elicit information for or provide information on one or more of medication reconciliation, diet, exercise, social determinants of health, living situation, assessment of severity of depression and anxiety symptomatology, substance use, assessment of cognitive availability, assessment of ability to perform activities of daily living, care pathways, clinical protocols, claims eligibility, claims adjustment, claims dispute, claims issues, pharmaceutical benefits, prior authorizations, and pre-admission, post-discharge, and ongoing care management factors, or the like.

In some embodiments, the method 400 may further generate summaries of the conversation held with the patient. These summaries may be generated, for example, at the end of the conversation (e.g., to summarize the conversation for the patient), at the start of the next conversations (e.g., to ground the patient or to provide efficient handoff to a human agent (e.g., before the human agent sees the patient)), or to other providers (e.g., in the context of a second opinion or to provide summaries for caretakers that may need to care for the patient). These summaries may further be personalized based on the intended audience (e.g., the summary may use different language depending on whether it's being delivered to the patient, a member of the care team, or a family member of the patient). The summaries may also be personalized based on, for example, the verbosity (e.g., level of detail, style (e.g. prose v bullet points, acronyms v spelled-out, etc.), level of education, demographic-based, health condition based (e.g. high contrast, font size for readability, etc.)). In some embodiments, the summaries may be topic-based instead of conversation based (e.g., for certain specialists so they receive only information relevant to their speciality). The topic-based conversations may also provide a summary of that topic through multiple conversations. The summaries may also aggregate information over multiple sessions and provide information on the trends for the patient. In some embodiments, the summaries may be provided as, for example, a filled out form or report on actions taken.

In some embodiments, the system may take drift awareness into account. For example, the system may be configured with conversational objectives (e.g., patient outcomes) and may try to accomplish those objectives using conversational tasks. The system may be configured to assess how well the conversational tasks led to the achievement of the conversational objectives and may update the conversational tasks based thereon. The system may further be configured to provide outputs based on the conversational tasks (e.g., present human agents with conversational tasks (e.g., best practices) to achieve certain conversational objectives).

According to an aspect, there is provided a method 400 to drive a conversation with a user. The method 400 including receiving conversational data from a user (block 402), embedding the conversational data, generating a reply using a response-generating AI to process the embedded conversational data and context from the knowledge base (block 406), and transmitting the generated reply. (block 410).

In some embodiments, the response-generating AI may include a knowledge base. In some embodiments, the response-generating AI may include an LLM. In some embodiments, the response-generating AI may include a multimodal. In some embodiments, the response-generating AI may include a world model.

In some embodiments, the method 400 further includes predicting whether the user has a physical, mental, or behavioural health condition or the severity of same using the conversational data.

In some embodiments, the method 400 further includes predicting one or more of global states of the user, moment-to-moment states of the user, context of a user environment. The global states of the user refer to states like conditions which are no likely to change during the course of the conversation (e.g., that the user has depression). Moment-to-moment states refer to less long lasting states that may be influenced by the course of the conversation (e.g., confusion, boredom, etc.). Context of the user environment may refer to ambient noise in the user's environment. These features may be used to further drive system behaviours.

In some embodiments, the method 400 further includes determining utility of the generated reply based on subsequent conversational data and updating the response-generating AI based on the utility of the generated reply.

In some embodiments, the method 400 further includes generating and actioning tasks based on the conversation.

In some embodiments, the tasks are generated and actioned based on patient information.

In some embodiments, the response-generating AI processes the embedded conversational data using cached conversational data, wherein the cached conversational data comprises prior embedded conversational data provided by the user.

In some embodiments, the context includes a conversational objective and a conversational task, the conversational task is used to generate the reply and the conversational objective is a goal of the conversation, and the method further includes determining utility of the generated reply in achieving the conversational objective based on subsequent conversational data and updating the conversational tasks based on the utility of the generated reply.

In some embodiments, transmitting the generated reply (block 410) comprises providing the generated reply to a human agent, wherein the generated reply is a suggested next response or action or direction.

In some embodiments, transmitting the generated reply (block 410) comprises delivering the generated reply to the user.

In some embodiments, the response-generating AI is configured to access electronic medical records.

In some embodiments, the response-generating AI is configured to use patient healthcare metadata.

In some embodiments, the conversational data is processed by an input guardrail to classify the conversational data as bad or good (block 404).

In some embodiments, the input guardrail processes the conversational data by determining that the conversational data exhibits one or more of unintelligibility, inappropriate behaviour, and inappropriate topic (block 404).

In some embodiments, the conversational data is embedded when the conversational data is classified as good or the input guardrail carries out remediation when the conversational data is classified as bad. In some embodiments, the input guardrail redirects the conversation to a human agent upon classifying the conversation data as bad. In some embodiments, the conversation data is classified as bad after remediation fails. In some embodiments, the human agent is provided with a summary of the conversation and/or a summary of a reason for the bad classification.

In some embodiments, the generated reply is processed by an output guardrail to classify the generated reply as good or bad (block 408).

In some embodiments, the output guardrail processes the generated reply by determining that the generated reply exhibits one or more of unresponsiveness, inaccuracy, harmful information, and inappropriate topic (block 408).

In some embodiments, the generated reply is transmitted to the user when the generated reply is classified as good or the output guardrail carries out remediation when the generated reply is classified as bad. In some embodiments, the output guardrail redirects the conversation to a human agent upon classifying the conversation data as bad. In some embodiments, the conversation data is classified as bad after remediation fails. In some embodiments, the human agent is provided with a summary of the conversation and/or a summary of a reason for the bad classification.

In some embodiments, the response-generating AI is pre-loaded with context from one or more of prior conversations with the user, health records about the user, conversational objectives.

In some embodiments, the conversational data is converted to text using an automatic speech recognition engine.

In some embodiments, the generated reply is converted to speech using a text-to-speech engine that can provide the generated speech as one of a plurality of custom voices.

In some embodiments, the method 400 is configured to elicit information for or provide information on one or more of medication reconciliation, diet, exercise, social determinants of health, living situation, assessment of severity of depression and anxiety symptomatology, substance use, assessment of cognitive availability, assessment of ability to perform activities of daily living, care pathways, clinical protocols, claims eligibility, claims adjustment, claims dispute, claims issues, pharmaceutical benefits, prior authorizations, and pre-admission, post-discharge, and ongoing care management factors, or the like.

In some embodiments, the method 400 is used for one or more of a medical follow up conversation, a patient intake conversation, an insurance intake conversation, or a troubleshooting technology conversation.

In some embodiments, the response-generating AI accesses a user profile comprising user preferences or personalizations to tailor the generated reply or the conversation. In some embodiments, the user profile may impact how the response-generating AI approaches the conversation as a whole (e.g., overall settings). In some embodiments, the user profile may impact how the response-generating AI formulates a particular reply.

In some embodiments, these preferences or personalizations may be provided by the user upon enrollment. In some embodiments, these preferences or personalizations may developed automatically as the method identifies what the user responds to (e.g., by assessing conversations and determining what types of replies elicited good input from the user on the next conversational turn). In some embodiments, the personalizations in the user profile are set by a healthcare professional in the clinical workflow. The health care professional may want the method to be carried out a certain way for their own use, and/or for that particular patient.

In some embodiments, the conversational data includes spoken language, text, or video.

In some embodiments, the method 400 is configured to be multilingual. In some embodiments, the method 400 further includes detecting a language of the conversational data prior to embedding the conversational data and using the detected language to embed the conversational data, select an embedding model, response-generating AI, input guardrail, or output guardrail, or translate the conversational data.

In some embodiments, the method 400 further includes assessing the user using a sensing engine.

In some embodiments, the method 400 further includes receiving a captured image of the user, processing the captured image with an image processing model to extract features from the captured image, processing the extracted features to generate a user assessment, and transmitting the user assessment to the response-generating AI.

Computational Implementation Details

Throughout the foregoing discussion, numerous references were made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface. The embodiments of the devices, systems and methods described herein can be implemented using, for example, cloud computing, services, and/or edge computing.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

The technical solution of embodiments may be in the form of a software product. The software product may be stored in a non-volatile or non-transitory storage medium, which can be a compact disk read-only memory (CD-ROM), a USB flash disk, a removable hard disk, or stored on a server (e.g., on an internal or external hard disc). The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

Figure 5:
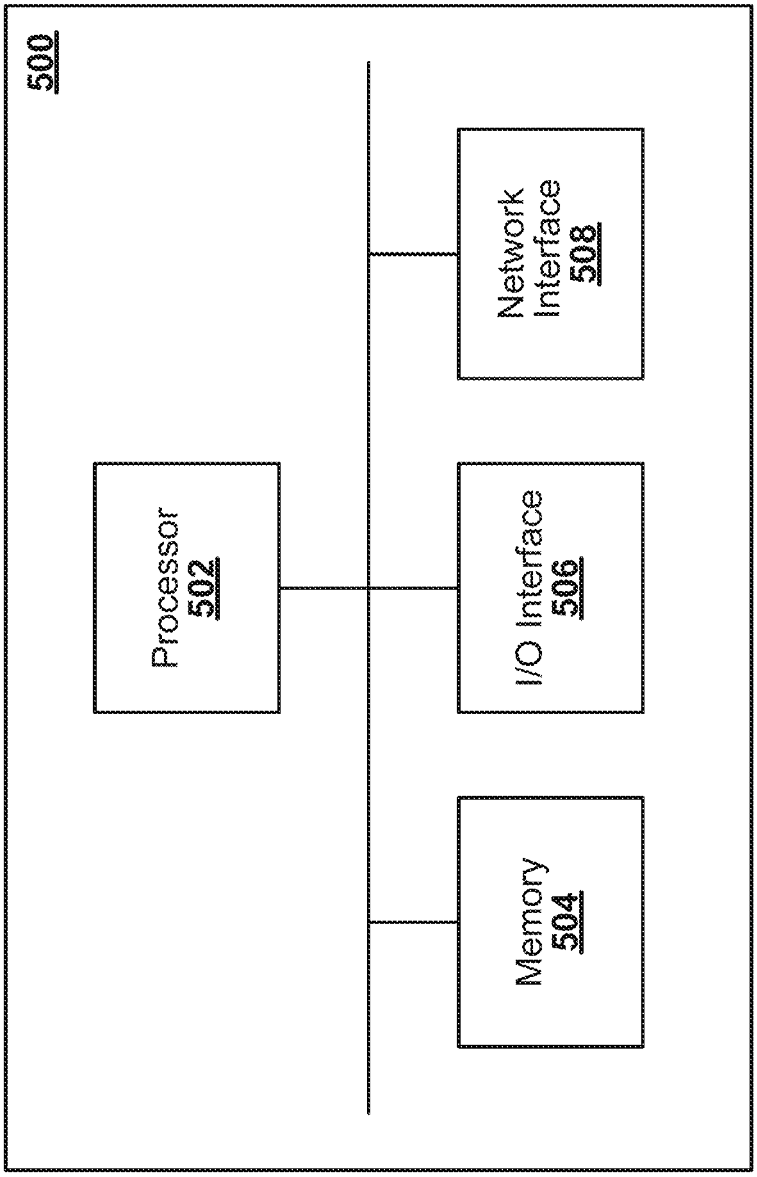
FIG. 5 shows a schematic diagram of a computing device, according to some embodiments.

FIG. 5 shows a schematic diagram of a computing device 500, according to some embodiments.

As depicted, computing device 500 includes at least one processor 502, memory 504, at least one I/O interface 506, and at least one network interface 508. Computing device 500 may be implemented as computing device 150 in systems 100 and 101 or the user device 170 and/or the agent device 180 in system 101.

For simplicity only one computing device 500 is shown but the system may include more computing devices 500 operable by users to access remote network resources and exchange data. The computing devices 500 may be the same or different types of devices. The computing device 500 has at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

For example, and without limitation, the computing device 500 may be a server, network appliance, set-top box, embedded device, computer expansion module, personal computer, laptop, personal data assistant, cellular telephone, smartphone device, UMPC tablets, video display terminal, gaming console, electronic reading device, and wireless hypermedia device or any other computing device capable of being configured to carry out the methods described herein Each processor 502 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory 504 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 506 enables computing device 500 to interconnect with one or more input devices, such as a keyboard, mouse, camera, touch screen and a microphone, or with one or more output devices such as a display screen and a speaker.

Each network interface 508 enables computing device 500 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Computing device 500 is operable to register and authenticate users (using a login, unique identifier, and password for example) prior to providing access to applications, a local network, network resources, other networks and network security devices. Computing devices 500 may serve one user or multiple users.

Implementation Details

While the foregoing has focused primarily on the healthcare context, systems and methods described herein may be applicable to other applications wherein an AI agent can carry out a conversation. For example, the AI agent may be configured to provide a user with guidance for using a product or accessing a service.

The foregoing discussion provides many example embodiments. Although each embodiment represents a single combination of inventive elements, other examples may include all possible combinations of the disclosed elements. Thus, if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

Although the embodiments have been described in detail, it should be understood that various changes, substitutions and alterations can be made herein without departing from the scope as defined herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the instant application is intended to include within its scope such processes, machines, manufacture, compositions of matter, means, methods, or steps.

As can be understood, the examples described above and illustrated are intended to be exemplary only.

What is claimed is:

1. A system to drive an orchestrated conversation interaction with a user, the system comprising:

a hardware processor comprising an orchestrator and a plurality of specialized AI agents, wherein each of the plurality of specialized AI agents comprise an LLM, a multimodal, and/or a world model;

hardware memory for storing instructions executable by the hardware processor; when executed by the hardware processor, the instructions cause the system to:

receive multimodal conversational data from a user;

decompose the multimodal conversational data into one or more sub-tasks in a task hierarchy via the orchestrator;

establish a standardized data interface for at least the multimodal conversation data;

execute the one or more sub-tasks by routing context retrieved via the standardized data interface and a virtual memory to at least one of the plurality of specialized AI agent;

aggregate outputs from the at least one specialized AI agent into a response;

transmit the response.

2. The system of claim 1, further comprising a vocal biomarker sensing engine configured to:

analyze vocal biomarkers to predict severity of a physical, mental, or behavioural health condition.

3. The system of claim 1, wherein the orchestrator updates a conversational task of the orchestrated conversation interaction.

4. The system of claim 1, wherein each of the specialized AI agents comprises at least one of a language model, multimodal, a world model, and/or a foundational model.

5. The system of claim 1, wherein the system is further configured to:

analyze visual clinical signs from captured imagery or video to determine biometric features;

generate a multimodal user assessment by fusing the biometric features with the conversational and data stream.

6. The system of claim 1, wherein the virtual memory comprises a hybrid architecture utilizing both a vector database for semantic similarity and a knowledge graph for symbolic relationship mapping.

7. The system of claim 1, further comprising a visual workflow interface configured to:

map pre-defined logic into a state-machine;

automatically generate executable code for the orchestrator to ensure transitions between conversation states occur only when protocol-specific conditions are met.

8. The system of claim 1, further comprising a multi-stage risk governance framework featuring synchronous and asynchronous input and output guardrails, wherein the hardware processor is configured to:

execute multidimensional risk profiling by independently evaluating user inputs and generated outputs against a taxonomy of non-binary risks, comprising at least clinical safety, PII exposure, and sentiment toxicity;

generate a composite severity vector by deriving a numerical severity score for each detected risk category within the taxonomy;

perform hierarchical conflict arbitration by applying an impact-priority hierarchy to the severity vector to select a primary risk trigger, prioritizing clinical safety or security over stylistic or contextual deviations; and initiating a dynamic response protocol by triggering an automated action specific to the level and category of the prioritized risk trigger.

9. The system of claim 8, wherein the dynamic response protocol differentiates between severity tiers using:

for high-severity triggers, an immediate execution of an override protocol that terminates the automated session or establishes a low-latency handoff to a human-in-the-loop (HITL) agent, transmitting the full conversation state and risk-vector analysis to said agent;

for moderate-severity triggers, the generation of a recovery directive transmitted to the worker AI, instructing the model to perform a "steerage correction" (such as a clarifying question or a refusal-with-redirection) without terminating the session; and for low-severity triggers, the logging of the event into a temporal metadata store for inclusion in an automated Post-Interaction Analytical Report (PIAR).

10. The system of claim 8, wherein the output guardrail includes an "Advice Grounding" module configured to compute a semantic divergence score between generated output and the grounded context retrieved via the MCP interface, triggering a Critical-State Override if the divergence exceeds a predetermined safety threshold.

11. The system of claim 9, wherein the recovery directive comprises a "Negative Token Constraint" injection, where the output guardrail provides the orchestrator with a list of prohibited semantic tokens or topics that the response generating engine must exclude from its subsequent iteration.

12. The system of claim 1, wherein the system processes the embedded conversational data using cached conversational data, wherein the cached conversational data comprises prior embedded conversational data provided by the user and other data gathered about the user.

13. The system of claim 1, wherein the specialized AI agents are specialized for specific domains or tasks, and the orchestrator evaluates the utility of specialized AI output against a global conversational objective or against a set of symbolic logic rules maintained by the state-based orchestrator prior to transmission.

14. The system of claim 1, wherein the orchestrator is configured to transition between conversation states ensuring that all conditions are met for entering a new stage.

15. The system of claim 1, wherein the orchestrator selects a specialized AI agents based on the identified call objectives, user input, and the current orchestrator state.

16. The system of claim 1, wherein the orchestration accesses a user profile to determine which specialized AI agent is best suited for the user's personalization preferences.

17. The system of claim 1, wherein the system detects a language of the conversational data prior to further processing and uses the detected language to:

embed the conversational data, select a specialized AI agent, an embedding model, input guardrail, or output guardrail tuned for the detected language, or translate the conversational data.

18. The system of claim 1, further comprising a sensing engine configured to:

receive a captured image of the user comprising a visual clinical sign or a physical, cognitive or mental health diagnostic artifact;

process the captured image with an image processing model to extract biometric or symptomatic features;

process the extracted features in combination with a concurrent data stream from a response-generating AI to generate a multimodal user assessment; and transmit the multimodal user assessment to the response-generating AI to trigger a protocol-specific modification of the AI's subsequent output.

19. The system of claim 1, wherein the system is further configured to:

aggregate context from prior conversation history, wherein the system applies a temporal summarization function to historical conversations and temporal non-linear decay function over other historical data, prioritizing details from recent interactions over historical data to determine current user status;

retrieve context from at least electronic health records, including longitudinal lab records and pharmacy-dispensing events; and generate a conversational objective, wherein the system is configured to dynamically adjust said conversational objective based on an affective state analysis derived from the summarized or weighted prior history, such that the interactional tone and goal are modified in response to detected user sentiment.

* * * * *